(12) United States Patent
Shen et al.

(10) Patent No.: US 11,655,496 B2
(45) Date of Patent: May 23, 2023

(54) AMPLIFICATION OF NUCLEIC ACIDS

(71) Applicant: LUMIRADX UK LTD, London (GB)

(72) Inventors: Daiwei Shen, London (GB); Bryan Kraynack, London (GB); Victor Perez, London (GB); Jarrod Provins, London (GB)

(73) Assignee: LumiraDx UK Ltd., London (GB)

( * ) Notice: Subject to any disclaimer, the term of this patent is extended or adjusted under 35 U.S.C. 154(b) by 0 days.

(21) Appl. No.: 16/956,552

(22) PCT Filed: Jan. 2, 2019

(86) PCT No.: PCT/GB2019/050005
§ 371 (c)(1),
(2) Date: Jun. 19, 2020

(87) PCT Pub. No.: WO2019/135074
PCT Pub. Date: Jul. 11, 2019

(65) Prior Publication Data
US 2021/0292826 A1 Sep. 23, 2021

(30) Foreign Application Priority Data
Jan. 4, 2018 (GB) ..................... 1800109

(51) Int. Cl.
*C12Q 1/6848* (2018.01)
*C12Q 1/6851* (2018.01)
*C12Q 1/6853* (2018.01)

(52) U.S. Cl.
CPC ......... *C12Q 1/6848* (2013.01); *C12Q 1/6851* (2013.01); *C12Q 1/6853* (2013.01); *C12Q 2521/101* (2013.01); *C12Q 2521/107* (2013.01); *C12Q 2521/307* (2013.01); *C12Q 2525/113* (2013.01); *C12Q 2525/131* (2013.01); *C12Q 2525/301* (2013.01); *C12Q 2527/101* (2013.01); *C12Q 2537/137* (2013.01)

(58) Field of Classification Search
CPC .. C12Q 1/6848; C12Q 1/6851; C12Q 1/6853; C12Q 2521/101; C12Q 2521/107; C12Q 2521/307; C12Q 2525/113; C12Q 2525/131; C12Q 2525/301; C12Q 2527/101; C12Q 2537/137; C12Q 1/6844
See application file for complete search history.

(56) References Cited

U.S. PATENT DOCUMENTS

| | | | |
|---|---|---|---|
| 6,191,267 B1 | 2/2001 | Kong et al. | |
| 6,794,142 B2 | 9/2004 | Laird et al. | |
| 8,143,006 B2 | 3/2012 | Kutyavin | |
| 8,313,932 B2 | 11/2012 | Moser et al. | |
| 8,822,154 B2 | 9/2014 | Orpana | |
| 9,428,781 B2 | 8/2016 | Cai et al. | |
| 9,670,531 B2 | 6/2017 | Caplin | |
| 9,689,031 B2 | 6/2017 | Maples et al. | |
| 9,845,495 B2 | 12/2017 | Komiya | |
| 10,036,077 B2 | 7/2018 | Komiya et al. | |
| 10,208,333 B2 | 2/2019 | Komiya et al. | |
| 10,316,358 B2 | 6/2019 | Cai et al. | |
| 10,329,601 B2 | 6/2019 | Shen et al. | |
| 10,604,790 B2 | 3/2020 | Komori et al. | |
| 10,927,393 B2 | 2/2021 | Zhang et al. | |
| 11,293,058 B2 | 4/2022 | Cai et al. | |
| 11,390,909 B2 | 7/2022 | Lambie et al. | |
| 2002/0025555 A1 | 2/2002 | Au-Young et al. | |
| 2002/0155573 A1 | 10/2002 | Lanes et al. | |
| 2003/0082590 A1 | 5/2003 | Van Ness et al. | |
| 2003/0211506 A1* | 11/2003 | Kong ............... | C12Q 2521/307 435/6.12 |
| 2005/0112631 A1 | 5/2005 | Piepenburg et al. | |
| 2006/0063175 A1 | 3/2006 | Xu et al. | |
| 2007/0231798 A1 | 10/2007 | Collins | |

(Continued)

FOREIGN PATENT DOCUMENTS

| | | |
|---|---|---|
| EP | 2699698 B9 | 1/2020 |
| JP | 2004-526432 A | 9/2004 |

(Continued)

OTHER PUBLICATIONS

Gao et al. Rapid isothermal detection assay: a probe amplification method for the detection of nucleic acids. Diagnostic Microbiology and Infectious Disease 2008; 60: 133-141 (Year: 2008).*
Nagamine et al. Isolation of Single-Stranded DNA from Loop-Mediated Isothermal Amplification Products. Biochemical and Biophysical Research Communications 2002; 290: 1195-1198 (Year: 2002).*
Wang et al. Technical aspects of nicking enzyme assisted amplification. Analyst 2018; 143: 1444-1453 (Year: 2018).*
International Preliminary Examining Report on Patentability dated Mar. 12, 2020, issued to corresponding International Application PCT/GB2019/050005.

(Continued)

*Primary Examiner* — Angela M. Bertagna
(74) *Attorney, Agent, or Firm* — Goodwin Procter LLP

(57) ABSTRACT

A method of performing a non-isothermal nucleic acid amplification reaction, the method comprising the steps of: (a) mixing a target sequence with one or more complementary single stranded primers in conditions which permit a hybridization event in which the primers hybridize to the target, which hybridization event, directly or indirectly, leads to the formation of a duplex structure comprising two nicking sites disposed at or near opposite ends of the duplex; and performing an amplification process by; (b) using a nicking enzyme to cause a nick at each of said nicking sites in the strands of the duplex; (c) using a polymerase to extend the nicked strands so as to form newly synthesized nucleic acid, which extension with the polymerase recreates nicking sites; (d) repeating steps (b) and (c) as desired so as to cause the production of multiple copies of the newly synthesized nucleic acid.

26 Claims, 25 Drawing Sheets

Specification includes a Sequence Listing.

(56) References Cited

U.S. PATENT DOCUMENTS

| | | | |
|---|---|---|---|
| 2009/0017453 A1* | 1/2009 | Maples | C12Q 1/686 |
| | | | 435/6.12 |
| 2009/0047678 A1 | 2/2009 | Kutyavin | |
| 2009/0092967 A1* | 4/2009 | Yao | C12Q 1/6844 |
| | | | 435/6.12 |
| 2009/0299047 A1 | 12/2009 | Korfhage et al. | |
| 2011/0165575 A1 | 7/2011 | Orpana | |
| 2012/0077252 A1 | 3/2012 | Picataggio et al. | |
| 2012/0208192 A1 | 8/2012 | Lee et al. | |
| 2015/0104788 A1 | 4/2015 | Shaffer et al. | |
| 2017/0183714 A1 | 6/2017 | Shen et al. | 1/689 |
| 2019/0194747 A1 | 6/2019 | Zhang et al. | |
| 2019/0226015 A1 | 7/2019 | Provins et al. | |
| 2020/0002756 A1 | 1/2020 | Lamble et al. | |
| 2021/0246487 A1 | 8/2021 | Lamble et al. | |
| 2021/0292826 A1 | 9/2021 | Shen et al. | |

FOREIGN PATENT DOCUMENTS

| | | |
|---|---|---|
| JP | 2008-520232 A | 6/2008 |
| JP | 2010-533494 A | 10/2010 |
| JP | 2014-513534 A | 6/2014 |
| JP | 2015-512654 A | 4/2015 |
| JP | 2015-518735 A | 7/2015 |
| RU | 2017821 C1 | 8/1994 |
| RU | 2260055 C2 | 9/2005 |
| WO | WO-1994/023055 A1 | 10/1994 |
| WO | WO-1999/037805 A1 | 7/1999 |
| WO | WO-2001/026583 A1 | 4/2001 |
| WO | WO-2003/048393 A1 | 6/2003 |
| WO | WO-2005/118144 A1 | 12/2005 |
| WO | WO-2005/118853 A2 | 12/2005 |
| WO | WO-2006/054172 A1 | 5/2006 |
| WO | WO-2007/028833 A2 | 3/2007 |
| WO | WO-2009/138564 A1 | 11/2009 |
| WO | WO-2011/030145 A1 | 3/2011 |
| WO | WO-2011/038197 A1 | 3/2011 |
| WO | WO-2012/083189 A2 | 6/2012 |
| WO | WO-2013/155056 A1 | 10/2013 |
| WO | WO 2017/027835 A1 | 2/2017 |
| WO | WO 2018/002649 A1 | 1/2018 |

OTHER PUBLICATIONS

Shi et al. "Nicking endonuclease-mediated isothermal exponential amplification for double-stranded DNA detection" Sensors and Actuators B: Chemical, 2015, vol. 222, p. 221-225.

Xu et al. "Real-time quantitative nicking endonuclease-mediated isothermal amplification with small molecular beacons" Analyst, 2016, vol. 141, No. 8, p. 2542-2552.

"Enzymatics Product Specifications P7140-HC-L Rev C", http://www.enzymatics.com/wp-content/uploads/2014/12/P7140-HC-L-REV-C-Manta-1.0-DNA-Polymerase-PSF-EFF-08MAY2014.pdf, May 8, 2014, 2 pages.

"Molecular Beacon Design" Public Health Research Institute, New Jersey Medical School—Rutgers, The State of University of New Jersey, https://web.archive.org/web/20160327223139/http://molecular-beacons.org/MB_SC_design.html; Mar. 27, 2016.

Alexandrov et al., (2012) "DNA breathing dynamics distinguish binding from nonbinding consensus sites fortranscription factor YY1 in cells," Nucl. Acids Res. 40(20):10116-10123.

Australian Examination Report for Application No. 2017287852, dated Aug. 30, 2022, 6 pages.

Barnes (1994) "PCR amplification of up to 35-kb DNA with high fidelity and high yield from λ bacteriophage templates," Proc. Natl. Acad. Sci. USA 91: 2216-2220.

Baskaran et al. (1996) "Uniform Amplification of a Mixture of Deoxyribonucleic Acids with Varying GC Content," Genome Res. 6:633-638.

Caballero et al. (1997) "Highly Sensitive Single-Step PCR Protocol for Diagnosis and Monitoring of Human Cytomegalovirus Infection in Renal Transplant Recipients," Journal of Clinical Microbiology 35(12):3192-3197.

Cheung (1996) "Whole genome amplification using a degenerate oligonucleotide primer allows hundreds of genotypes to be performed on less than one nanogram of genomic DNA," Proceedings of the National Academy of Sciences, USA 93:14676-14679.

Compton (1991) "Nucleic acid sequence-based amplification," Nature 350:91-92.

Decision to Grant a Patent for Invention dated Sep. 24, 2021, issued by the Federal Service for Intellectual Property in corresponding application RU 2019101504/10(002569).

Eggerding (1995) "A One-Step Coupled Amplification and Oligonucleotide Ligation Procedure for Multiple Genetic Typing," Genome Res. 4:337-345.

Ehses et al. (2005) "Optimization and design of oligonucleotide setup for strand displacement amplification," Journal of Biochemical and Biophysical Methods 63:170-186.

Frackman et al. (1998) "Betaine and DMSO: Enhancing Agents for PCR," Promega Notes 65:27.

Gao et al. (2008) "Rapid isothermal detection assay: a probe amplification method for the detection of nucleic acids" Diagnostic Microbiology and Infectious Disease 60:133-141.

Google Definition—"Subject", https://www.bing.com/search?q=subject&form=SWAUA2, undated, 1 page.

Henke et al. (1997) "Betaine improves the PCR amplification of GC-rich DNA sequences," Nucleic Acids Research 25(19):3957-3958.

Hutton et al. (1975) "Activity of Endonuclease $S_1$ in Denaturing Solvents: Dimethysulfoxide, Dimethylformamide, Formamide and Formaldehyde," Biochem. and Biophys. Research Comm. 66(3):942-948.

Iakobashvili et al. (1999) "Low temperature cycled PCR protocol for Klenow fragment of DNA polymerase I in the presence of proline," Nucleic Acid Research 27(6):1566-1568.

International Search Report dated Sep. 12, 2017, issued to International Application No. PCT/GB2017/051927.

J. R. Buser et al. "Precision chemical heating for diagnostic devices", Lab Chip, 2015, pp. 4423-4432.

Jensen et al. (2010) "DMSO and Betaine Greatly Improve Amplification of GC-Rich Constructs in De Novo Synthesis," PLoSOne 5(6):1-5.

Joneja et al. (2011) "Linear nicking endonuclease-mediated strand-displacement DNA amplification," Analytical Biochemistry 414:58-69.

Kim et al. (1988) "Recombinant fragment assay for gene targeting based on the polymerase chain reaction," Nucleic Acids Research 16(18):8887-8903.

Korbie et al. (2008) "Touchdown PCR for increased specificity and sensitivity in PCR amplification," Nature Protocols 3(9):1452-1456.

Kurn et al., (2005) "Novel Isothermal, Linear Nucleic Acid Amplification Systems for Highly Multiplexed Applications," Clin. Chem. 51 (10):1973-81.

Liu et al. (1998) "Subcycling-PCR for Multiplex Long-Distance Amplification of Regions with High and Low GC Content: Application to the Inversion Hotspot in the Factor VIII Gene," BioTechniques 25:1022-1028.

Lizardi et al. (1998) "Mutation detection and single-molecule counting using isothermal rolling-circle amplification," Nature Genetics 19:225-232.

Masny et al. (2003) "Ligation medicated PCR performed at low denaturation temperatures - PCR melting profiles," Nucleic Acids Research 31(18):e114.

Mecklenburg (1996) Design of High-Annealing-Temperature PCR Primers and Their use in the Development of a Versatile Low-Copy-No. Amplification Protocol, Advances in Molecular and Cell Biology vol. 15, Abstract only.

Nagamine et al. (2002) "Isolation of Single-Stranded DNA from Loop-Mediated Isothermal Amplification Products" Biochemical and Biophysical Research Communications 290:1195-1198.

New England Biolabs "Effect of Various Temperatures on Nicking Endonucleases," Available at https://www.neb.com/tools-and-resources/selection-charts/effect-of-various-temperatures-on-nicking-endonucleases. Accessed on Feb. 10, 2021. (Year: No. Date) 2 pages.

(56) References Cited

OTHER PUBLICATIONS

Notice of Opposition dated Jul. 7, 2021 issued by the European Patent Office in connection with European Patent No. EP3478853.
Notomi et al. (2000) "Loop-mediated isothermal amplification of DNA," Nucl. Acids Res. 28(12):e63.
Piepenberg et al. (2006) "DNA Detection Using Recombination Proteins," PLoS Biology 4(7):e204 1115-1121.
Roux (2002) "Single-Step PCR Optimization Using Touchdown and Stepdown PCR Programming," Methods in Molecular Biology 192:31-36.
Roux (2009) "Optimization and Troubleshooting in PCR" Cold Spring Harbor Protocols 4(4):7 pages.
Russian Office Action dated Nov. 30, 2020, to Russian Application No. 2019101504/04.
Sarkar et al. (1990) "Formamide can dramatically improve the specificity of PCR," Nucleic Acid Research 18(24):7465.
Shuchard et al. (1993) "Two-Step "Hot" PCR Amplification of GC-Rich Avian e-mye Sequences," BioTechniques 14(3):390-394.
Su et al. (1996) "Reduced extension temperatures required for PCR amplification of extremely A+ T-rich DNA," Nucleic Acids Research, 24(8)1574-1575.
Van Ness et al. (2003) "Isothermal reactions for the amplification of oligonucleotides," Proceedings of the National Academy of Sciences 100(8):4504-4509.
Varadaraj et al. (1994) "Denaturants or cosolvents improve the specificity of PCR amplification of a G+C-rich DNA using genetically engineered DNA polymerases," Gene 140:1-5.
Vaughn et al. (1998) "A novel process for mutation detection using uracil DNA-glycosylase," Nucleic Acids Research 26:810-815.
Vincent et al., (2004) "Helicase-dependent isothermal DNA amplification," EMBO Rep. 5(8)795-800.
Von Hippel et al., (2013) "50 years of DNA 'Breathing': Reflections on Old and New Approaches," Biopolymers 99(12):923-954.
Walker et al., (1992) "Strand displacement amplification-an isothermal, in vitro DNA amplification technique," Nucl. Acids Res. 20(7):1691-1696.
Wang DG, et al. (2015) Two methods for increased specificity and sensitivity in loop-mediated isothermal amplification. Molecules. 20(4):6048-59.
Wang et al. (2018) "Technical aspects of nicking enzyme assisted amplification" Analyst 143:1444-1453.
Weighardt et al. (1993) "A Simple Procedure for Enhancing PCR Specificity," PCR methods and Applications, Cold Spring Harbor Laboratory Press 3(1):77-81.
Written Opinion of the International Searching Authority dated Jan. 4, 2018, issued to International Application No. PCT/GB2017/051927.
Zhang et al. (2009) "Parallel DNA amplification by convective polymerase chain reaction with various annealing temperatures on a thermal gradient device," Analytical Biochemistry 387(1), Abstract only.
Zheleznaya et al. (2009) "Nicking Endonucleases," Biochemistry (Moscow) 74(13):1457-1466.

* cited by examiner

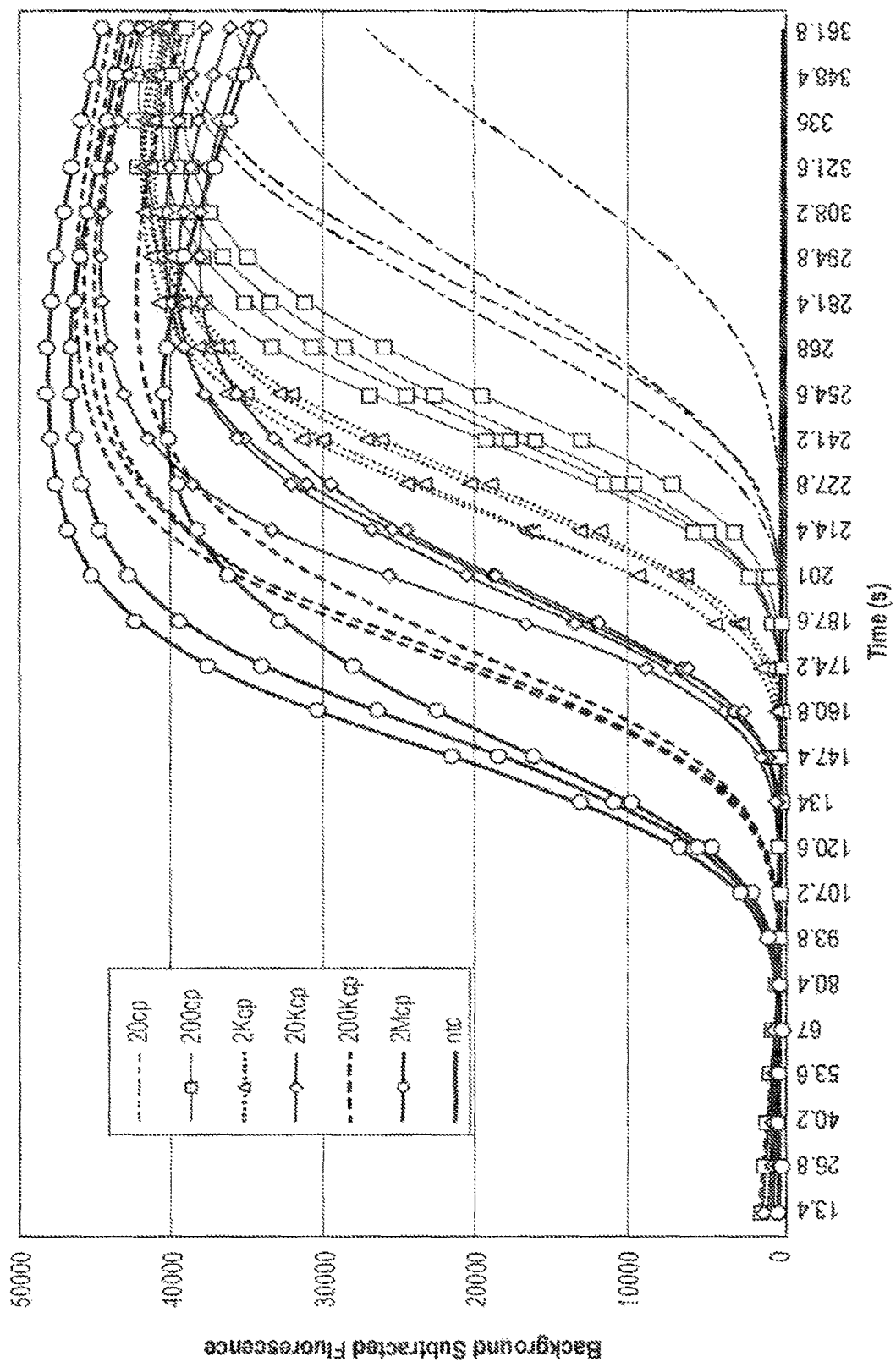

Example Quantitative Test Unknown Samples Summary

Table 2

| Sample | Copy # Added | qPCR Estimated Copy # | qSTAR Estimated Copy # |
|---|---|---|---|
| UNK01 | 250 | 114 | 276 |
| UNK02 | 50000 | 45848 | 75699 |
| UNK03 | 0 | 0 | 0 |
| UNK04 | 100000 | 96886 | 140611 |
| UNK05 | 8000 | 5816 | 10630 |

FIG. 13B

SEQUENCE LISTING

<160> NUMBER OF SEQ ID NOS: 16

<210> SEQ ID NO 1
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 1
cgactccata tggagtcgat ttccccgaat ta                         32

<210> SEQ ID NO 2
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 2
ggactccaca cggagtcttt ttccttgttt ac                         32

<210> SEQ ID NO 3
<211> LENGTH: 33
<212> TYPE: DNA
<213> ORGANISM: Artificial sequence

```
<220> FEATURE:
<223> OTHER INFORMATION: Synthetic oligonucleotide

<400> SEQUENCE: 3
ccattccttg tttactcgta tttttaggaa tgg                                33

<210> SEQ ID NO 4
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 4
accgcgcgca ccgagtctgt cggcagcacc gct                                33

<210> SEQ ID NO 5
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 5
agcggtgctg ccgaca                                                   16

<210> SEQ ID NO 6
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 6
ggtgcgcgcg gt                                                       12

<210> SEQ ID NO 7
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 7
accgcgcgca ccgagtctgt cggca                                         25

<210> SEQ ID NO 8
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 8
ctgccgacag actcggtgcg cgcggt                                        26

<210> SEQ ID NO 9
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 9
aaaaagattt ccccgaatta g                                             21
```

<210> SEQ ID NO 10
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 10
agttactttt tccttgttt                                                   19

<210> SEQ ID NO 11
<211> LENGTH: 34
<212> TYPE: DNA
<213> ORGANISM: Artificial sequence
<220> FEATURE:
<223> OTHER INFORMATION: Synthetic oligonucleotide

<400> SEQUENCE: 11
tgactccaca cggagtcata aatcctgctg cmua                                  34

<210> SEQ ID NO 12
<211> LENGTH: 33
<212> TYPE: DNA
<213> ORGANISM: Artificial sequence
<220> FEATURE:
<223> OTHER INFORMATION: Synrhetic oligonucleotide

<400> SEQUENCE: 12
tgactccaca cggagtcaga accaacaaga aga                                   33

<210> SEQ ID NO 13
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 13
tgaggtgctg ctatgcctca                                                  20

<210> SEQ ID NO 14
<211> LENGTH: 38
<212> TYPE: DNA
<213> ORGANISM: Artificial sequence
<220> FEATURE:
<223> OTHER INFORMATION: Synthetic oliognucleotide

<400> SEQUENCE: 14
ggactcgaca ccgagtccag ttacgattmt mgmtmtmg                              38

<210> SEQ ID NO 15
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 15
ggactccata tggagtccta cggctccgct ttt                                   33

<210> SEQ ID NO 16
<211> LENGTH: 29
<212> TYPE: DNA
<213> ORGANISM: Artificial sequence
<220> FEATURE:
<223> OTHER INFORMATION: Synthetic oligonucleotide

```
<400> SEQUENCE: 16
gctgcgttcc aattcgcctt tttcgcagc                                                29
```

AMPLIFICATION OF NUCLEIC ACIDS

CROSS-REFERENCE TO RELATED APPLICATIONS

This application is a national stage of International Application No. PCT/GB2019/050005, filed Jan. 2, 2019, which claims the benefit of Great Britain Application No. 1800109.9, filed Jan. 4, 2018, in the European Patent Office, the disclosures of which are incorporated herein by reference.

SEQUENCE LISTING

The instant application contains a Sequence Listing which has been submitted electronically in ASCII format and is hereby incorporated by reference in its entirety. Said ASCII copy, created on Jun. 17, 2020, is named seqlisting_0851_1005.txt and is 3,410 bytes in size.

FIELD OF THE INVENTION

The present invention relates to a method of amplifying a nucleic acid molecule, especially in a quantitative manner.

BACKGROUND OF THE INVENTION

The polymerase chain reaction (PCR) is well-known and a standard technique used to amplify nucleic acid molecules. The amplified products of the PCR are detected at the end of the reaction. The amount of product tends to reach a plateau level, which does not increase if the reaction mixture is left longer. As a result, in conventional PCR the amount of product does not necessarily correlate with the concentration of amplification target sequence present in the mixture at the outset.

In order to obtain quantitative data, quantitative PCR ("qPCR") is performed, in which the amount of amplification product produced is monitored or detected in real time (hence qPCR is also referred to as "Real-Time PCR" or even "RT-PCR", although this latter abbreviation is unhelpful as it can be confused with Reverse Transcriptase-PCR), whilst the reaction is still actively amplifying the target sequence.

Typically, amplified nucleic acid is detected by its interaction with a label entity (usually the label is a fluorophore). This interaction may be non-specific (i.e. the label entity binds to essentially any double-stranded DNA molecule) or specific (i.e. the label entity interacts in a nucleotide-sequence dependent manner preferentially with a specific nucleic acid sequence present in the desired amplification product).

An example of a non-specific label entity is the dye SYBR® Green. A specific label entity (e.g. a labelled probe molecule) might be, for example, a "molecular beacon", which fluoresces when it undergoes a conformational change induced by hybridisation to a target sequence.

Thus, monitoring the level of fluorescence observed in real time, during the PCR, allows the generation of quantitative data, in which the amount of amplification product (as measured by detection of fluorescence, for example) correlates with the concentration of the amplification target molecule in the sample.

qPCR as described in U.S. Pat. No. 6,814,943 utilises temperature ranges for cycling. Typically for qPCR the following procedure is undertaken: denaturation around 95° C., annealing around 55° C., extension around 70° C. These are large temperature changes (about 40° C. difference between maximum and minimum temperatures). As a result qPCR, like "normal" non-quantitative PCR, requires the use of relatively sophisticated thermal cycling apparatus. Thus, whilst qPCR is highly useful in a research context (e.g. quantification of gene expression), it is not readily applicable to point-of care ("PoC") diagnostic tests and the like.

Many nucleic acid amplification techniques have been devised, which are performed isothermally, in order to avoid the need for thermal cycling. A non-exhaustive list of such amplification techniques includes: signal mediated amplification of RNA technology ("SMART"; WO 99/037805); nucleic acid sequence based amplification ("NASBA" Compton 1991 Nature 350, 91-92); rolling circle amplification ("RCA" e.g. see Lizardi et al., 1998 Nature Genetics 19, 225-232); loop-mediated amplification ("LAMP" see Notomi et al., 2000 Nucl. Acids Res. 28, (12) e63); recombinase polymerase amplification ("RPA" see Piepenberg et al., 2006 PLoS Biology 4 (7) e204); strand displacement amplification ("SDA"); helicase-dependent amplification ("HDA" Vincent et al., 2004 EMBO Rep. 5, 795-800): transcription mediated amplification ("TMA"), single primer isothermal amplification ("SPIA" see Kurn et al., 2005 Clinical Chemistry 51, 1973-81); self-sustained sequence replication ("3SR"); and nicking enzyme amplification reaction ("NEAR").

SDA is a technique (disclosed by Walker et al., 1992 Nucl. Acids Res. 20, 1691-1696) which involves the use of a pair of primers comprising a target-complementary portion and, 5' of the target-complementary portion, a recognition and cutting site for an endonuclease. The primers hybridise to respective complementary single stranded target molecules. The 3' end of the target strands are extended using a reaction mix including a DNA polymerase and at least one modified nucleotide triphosphate, using the primer as template (and likewise, the 3' ends of the primers are extended using the target as template).

The extension of the target strands generates a double stranded recognition site for the endonuclease. However, because the target is extended using a modified triphosphate, the endonuclease does not cleave both strands but instead makes a single stranded nick in the primer. The 3' ends at the nicks are then extended by the DNA polymerase (typically Klenow fragment of DNA polymerase I, which lacks an exonuclease activity). As the nicked primers are extended, they displace the initially-produced extension product. The displaced product is then free to hybridise to the opposite primer, since it essentially replicates the sequence of the target for the opposite primer. In this way, exponential amplification of both strands of the target sequence is achieved.

The amplification stage of the SDA process is essentially isothermal—typically performed at 37° C.—the optimum temperature for the endonuclease and the polymerase. However, before reaching the amplification stage it is necessary to completely dissociate the double stranded target into its constituent single strands, in order to allow the pair of primers to hybridise to their complementary target strands.

This dissociation, or "melting" is normally accomplished by heating the double stranded target to a high temperature—usually about 90° C.—in order to break the hydrogen bonds between the two strands of the target. The reaction mix is then cooled to allow the addition of the enzymes which are necessary for the amplification reaction. Because of the high temperature used to generate the single stranded targets, the SDA technique is not ideally suited to a PoC context.

U.S. Pat. No. 6,191,267 discloses the cloning and expression of N.BstNBI nicking enzyme and its use in SDA, in place of restriction endonucleases and modified triphosphates.

Another amplification technique, which is similar to SDA, is Nicking Enzyme Amplification Reaction (or "NEAR").

In 'NEAR' (e.g. as disclosed in US2009/0017453 and EP 2,181,196), forward and reverse primers (referred to in US 2009/0017453 and EP 2,181,196 as "templates") hybridise to respective strands of a double stranded target and are extended. Further copies of the forward and reverse primers (present in excess) hybridise to the extension product of the opposite primer and are themselves extended, creating an "amplification duplex". Each amplification duplex so formed comprises a nicking site towards the 5' end of each strand, which is nicked by a nicking enzyme, allowing the synthesis of further extension products. The previously synthesised extension products can meanwhile hybridise with further copies of the complementary primers, causing the primers to be extended and thereby creating further copies of the "amplification duplex". In this way, exponential amplification can be achieved.

NEAR differs from SDA, in particular, in that no initial thermal dissociation step is required. The initial primer/target hybridisation event needed to trigger the amplification process takes place whilst the target is still substantially double stranded: it is thought that the initial primer/target hybridisation takes advantage of localised dissociation of the target strands—a phenomenon known as "breathing" (see Alexandrov et al., 2012 Nucl. Acids Res. and review by Von Hippel et al., 2013 Biopolymers 99 (12), 923-954). Breathing is the localised and transient loosening of the base pairing between strands of DNA. The melting temperature (Tm) of the initial primer/target heteroduplex is typically much lower than the reaction temperature, so the tendency is for the primer to dissociate, but transient hybridisation lasts long enough for the polymerase to extend the primer, which increases the Tm of the heteroduplex, and stabilises it.

The amplification stage in NEAR is performed isothermally, at a constant temperature. Indeed, it is conventional to perform both the initial target/primer hybridisation, and the subsequent amplification rounds, at the same constant temperature, usually in the range 54 to 56° C.

Avoiding the need for thermal cycling means that NEAR is potentially more useful than PCR in PoC contexts. In addition, synthesis of significant amounts of amplification product, even when starting from a very low copy number of target molecules (e.g. as few as 10 double stranded target molecules), can be achieved.

WO 2011/030145 (Enigma Diagnostics Limited) discloses the idea of performing an "isothermal" nucleic acid amplification (NASBA, SDA, TMA, LAMP, Q-beta replicase, rolling circle amplification and 3SR are specifically mentioned) at a predetermined temperature initially, changing the temperature of the reaction, and then allowing the temperature to return to the predetermined temperature at least once during the reaction. More specifically the document suggests causing a temperature oscillation or "wobble" during the amplification reaction, which is said to "improve the overall time to completion and signal-to-noise [ratio] of the assay". The idea was explored experimentally using the TMA amplification technique to amplify bacterial RNA. The results showed that, whilst the "wobbled" reaction started to amplify target sooner than the truly isothermal reaction, there was still a delay of about 13 minutes before the fluorescence signal rose above the initial background level.

The present invention aims to provide a novel nucleic acid amplification technique having one or more advantages over existing techniques and which, in particular, is able to generate quantitative data.

SUMMARY OF THE INVENTION

In a first aspect, the present invention provides a method of performing a non-isothermal nucleic acid amplification reaction, the method comprising the steps of:

(a) mixing a target sequence with one or more complementary single stranded primers in conditions which permit a hybridisation event in which the primers hybridise to the target, which hybridisation event, directly or indirectly, leads to the formation of a duplex structure comprising two nicking sites disposed at or near opposite ends of the duplex; and performing an amplification process by;

(b) using a nicking enzyme to cause a nick at each of said nicking sites in the strands of the duplex;

(c) using a polymerase to extend the nicked strands to as to form newly synthesised nucleic acid, which extension with the polymerase recreates nicking sites;

(d) repeating steps (b) and (c) as desired so as to cause the production of multiple copies of the newly synthesised nucleic acid;

characterised in that the temperature at which the method is performed is non-isothermal, and subject to shuttling, a plurality of times, between an upper temperature and a lower temperature during the amplification process of steps (b)-(d), wherein at the upper temperature, one of said polymerase or nicking enzyme is more active than the other of said enzymes, such that there is a disparity in the activity of the enzymes, and at the lower temperature the disparity in the activity of the enzymes is reduced or reversed.

The nicking enzyme and the polymerase will have certain rates of catalytic activity. These will vary with temperature. The respective rates of activity of the enzymes (in terms of moles of substrate reacted per unit time per mg of enzyme at a given substrate concentration) will usually be different at a particular temperature. Each enzyme will have an optimum temperature at which its rate of activity is maximal. Generally speaking, the further the temperature of a reaction mixture is from an enzyme's optimum temperature, the slower the rate of activity of the enzyme.

The relative favouring of one enzyme over another (so as to achieve a disparity between the rate of activity of the polymerase and nicking-enzyme) can be obtained by using temperature conditions which permit greater activity of one of said enzymes than the other, or by using temperature conditions which are less favourable for one of the enzymes than the other.

By way of explanation, the disparity in the activity of the enzymes is considered to be "reversed" if, at the upper temperature one of the enzymes has a higher activity than the other enzyme, whilst at the lower temperature the other of said enzymes has a higher activity.

In other embodiments, the disparity in the activity of the enzymes at the upper and lower temperature is not reversed, but merely reduced. Typically the disparity in activity between the enzymes at one of said upper or lower temperature is reduced by at least 5% at the lower or upper temperature, as appropriate. More preferably the disparity is reduced by at least 10%, at least 15%, at least 20%, at least 25%, at least 30%, at least 35%, at least 40% or at least 45%. Most preferably the disparity is reduced by at least 50%, or at least 75%.

For the avoidance of doubt, "enzyme activity" in this context refers to "specific enzyme activity" (pmol substrate reacted min$^{-1}$mg$^{-1}$ enzyme), measured under the same conditions for the polymerase and the nicking enzyme.

In one preferred embodiment, the method of the first aspect of the invention comprises the use of a set of temperature conditions wherein at one of said upper and lower temperatures, both the nicking enzyme and the polymerase are substantially active (i.e. for present purposes, operating at a rate which is at least 50%, or higher, of the rate at which the enzyme would operate at its optimum temperature in otherwise identical conditions; preferably at 60% or higher, more preferably at 65% or higher; and most preferably at 70%, or higher, of its rate of activity at its optimum temperature); whilst at the other of said lower and upper temperatures (as the case may be), at least one of either the nicking enzyme or polymerase is substantially inhibited (i.e. operating at 49% or less of the rate at which the enzyme would operate at its optimum temperature in otherwise identical conditions; preferably less than 45%, more preferably less than 40%; and most preferably less than 35% of its rate of activity at its optimum temperature). In some embodiments the nicking enzyme is substantially inhibited at one of the upper or lower temperature. In some embodiments the nicking enzyme is substantially inhibited at the upper temperature.

In some embodiments the polymerase is substantially inhibited at one of the upper or lower temperature. In some embodiments the polymerase is substantially inhibited at the lower temperature; in other embodiments the polymerase is substantially inhibited at the upper temperature.

The length of time that the reaction mixture is held constant at the upper temperature, or at the lower temperature, may be referred to as the "dwell time", and to distinguish between them, one can refer to the "upper temperature dwell time" and the "lower temperature dwell time". The upper temperature dwell time and the lower temperature dwell time may be the same, or may be different. If different, the upper temperature dwell time may be longer or shorter than the lower temperature dwell time.

A critical parameter for quantitative analysis is how well the generated data fit a regression line, known as the coefficient of determination ($R^2$). Data are not considered quantitative if they have a poor coefficient of determination. For present purposes, data are considered quantitative if their coefficient of determination is equal to or greater than 0.850, typically equal to or greater than 0.900, preferably equal to or greater than 0.950, more preferably equal to or greater than 0.975, and most preferably equal to or greater than 0.990. The coefficient of determination ($R^2$) may conveniently be calculated using the method described by Pfaffl (2001, Nucl. Acids Res. 29 (9) e45).

Accordingly, a method of performing a nucleic acid amplification reaction and/or analysing a sample by means of such a reaction, is considered quantitative if it generates data which are quantitative according to the foregoing definition. Surprisingly, the method of the invention is able to generate quantitative data.

The amplification reaction of the invention is preferably performed in a manner generally superficially similar to that known as "NEAR" and disclosed in EP 2,181,196. However importantly, and quite unlike the NEAR technique, the present method is performed non-isothermally and involves repeated shuttling between an upper and a lower temperature.

In some embodiments the upper temperature may relatively favour the activity of the polymerase over that of the nicking enzyme, and the lower temperature will relatively favour the activity of the nicking enzyme over that of the polymerase. Surprisingly however, the inventors have found that the "temperature preferences" can be fully reversed, such that in some embodiments the upper temperature may relatively favour the activity of the nicking enzyme over that of the polymerase and the lower temperature may relatively favour the activity of the polymerase over that of the nicking enzyme.

Without being bound by any particular theory, it appears that by appropriate selection of a polymerase and a nicking enzyme with different temperature optima it is possible to have the upper temperature of the amplification reaction relatively favour either the polymerase or the nicking enzyme, and vice versa in relation to the lower temperature of the amplification reaction.

Without being bound by any particular theory, it is further hypothesised by the inventors that a possible mechanism for the rapid amplification achieved by the method of the present invention invokes causing a reduction in the activity of one or other of the nicking enzyme or the polymerase, by using a temperature which is considerably sub-optimal for the enzyme, leading to an accumulation of potential substrate molecules. When the temperature of the reaction mixture is adjusted to a temperature which is closer to optimal for the enzyme in question, the activity of the enzyme is significantly enhanced which, in conjunction with the relatively high concentration of accumulated substrate, results in a greatly accelerated rate of reaction. In simplistic terms, the average rate of reaction of this "quick/slow" format is greater than the average rate of reaction achievable using a "steady state" system with a constant, or relatively slowly-changing, temperature.

It will be apparent to the person skilled in the art that it may be desirable that the optimum temperature of the nicking enzyme be different (higher or lower) from that of the polymerase used in the method of the invention.

Typically the respective optimum temperatures of the nicking enzyme and the polymerase should differ by at least 1° C., preferably by at least 3° C., more preferably by at least 5° C., and most preferably by at least 10° C. Conveniently the respective optimum temperatures will differ by an amount in the range 10-30° C., more typically in the range 10-25° C.

There is no absolute requirement that the optimum temperature of the polymerase is higher than that of the nicking enzyme. Thus, for example, there are embodiments of the invention in which the reaction utilises a polymerase (e.g. obtained from a psychrophilic source) which has a lower optimum temperature than that of the nicking enzyme, whilst in other embodiments the polymerase has a higher optimum temperature than that of the nicking enzyme.

Thus, in general, the upper temperature is preferably selected so as to relatively favour a sequence-specific polymerase-mediated extension phase (i.e. formation of a complex between the polymerase and the hybridised initial primer/target duplex, followed by the polymerase-mediated extension of the primer; and almost immediately thereafter, extension of the opposite primer hybridised to the extended initial primer). The use of an elevated temperature tends to reduce primer dimer formation and aberrant amplification of undesired mis-hybridised duplexes. The polymerase is conveniently selected so as to be sufficiently stable at the upper temperature as to perform the primer extension throughout the duration of the reaction without significant diminution of activity. For present purposes, "significant diminution" means a decline of 50% or more in specific enzyme activity of the polymerase.

The lower temperature is preferably selected so as to permit the nicking enzyme to cut the nick sites on the duplex. The nicking enzyme typically (but not necessarily) has an optimum temperature which is lower than that of the polymerase, hence the transition to the lower temperature typically moves the reaction temperature closer to the optimum temperature of the nicking enzyme.

In some embodiments of the method of the invention as exemplified herein, the upper temperature is preferably in the range 50.0-64.0° C., more preferably in the range 55.0-63.0° C. However, those skilled in the art will appreciate that the preferred "upper temperature" may vary depending on the identity of the enzymes present and possibly also on the length and sequence of the primers and/or the intended amplification target.

For example, in some embodiments, the upper temperature could be as high as 68° C. but, in those conditions:
 (a) one would normally wish to use a thermal shuttling profile with a reduced dwell time at the upper temperature (e.g. no more than about 1-2 seconds per shuttle); and
 (b) such a high upper temperature works well only with relatively high copy number of target sequence in the sample (e.g. about $10^3$ copies or higher).

In the method of the invention as exemplified herein, the lower temperature is preferably in the range 20.0-58.5° C., more preferably in the range 35.0-57.9° C.

Again, however, as noted above, those skilled in the art will appreciate that the preferred "lower temperature" may vary depending on the identity of the enzymes present, and possibly also the length and sequence of the primers and/or the intended amplification target.

As a general rule, as is well known to those skilled in the art, the stringency of hybridisation increases with increasing temperature (within limits), such that higher temperatures will generally reduce non-specific interactions such as between mis-matched primers and non-complementary polynucleotide sequences present in the sample. Thus a higher temperature for hybridisation reactions will normally be preferable to a lower temperature, as long as the temperature does not exceed the melting temperature of the specific primer/target sequence hybridisation.

Desirably, in preferred embodiments the difference in temperature between the upper temperature and the lower temperature will be in the range 4-12° C., more preferably in the range 4-10° C., and most preferably in the range 4-8° C.

Generally, although not necessarily, it may be preferred for the reaction mixture to be held at the upper temperature for a shorter period of time (the "dwell time") than that for the lower temperature, although the "dwell time" at the upper and lower temperatures could be equal or even, in other embodiments, the dwell time at the upper temperature might be longer than that for the lower temperature—although this is generally not preferred.

It is envisaged that, within certain limits, in general the higher the frequency of the thermal shuttling, the faster the amplification reaction will proceed. Thus the duration of one complete thermal shuttle will preferably be less than 3.0 minutes, more preferably less than 2.0 minutes, and most preferably less than 1.0 minute. Most advantageously, the duration of a thermal shuttle will be less than 45 seconds and most preferably less than 30 seconds. A minimum duration of a thermal shuttle will typically be at least 1 second, preferably at least 2 seconds, and more preferably at least 5 seconds. A typical preferred duration for one complete thermal shuttle will be between 5 and 30 seconds, preferably between 5 and 20 seconds, and most preferably between 5 and 15 seconds.

A typical preferred dwell time at the upper temperature might be between 1 and 10 seconds, preferably 1-5 seconds, and most preferably 1-3 seconds.

A typical preferred dwell time at the lower temperature might be between 2 and 40 seconds, more preferably between 3 and 30 seconds, and most preferably between 3 and 15 seconds.

The time taken to shuttle between the upper and lower temperatures is preferably kept substantially to a minimum. It is envisaged that the typical volume of an amplification reaction mixture will be less than 500 μl, probably less than 250 μl and, given that the upper and lower temperatures will typically be less than 10° C. apart, it should be possible and preferred to transition from the lower to upper temperature (or vice versa) in about 0.5-10.0 seconds, more preferably in the range 1-5 seconds.

Conveniently the duration/temperature profile of each of the plurality of shuttles is essentially identical—this simplifies performance of the method. Thus, for example, each of the plurality of thermal shuttles will conveniently have the same overall duration, the same dwell time at the upper temperature, the same dwell time at the lower temperature, etc.

However, in some embodiments (especially those in which there is real-time detection of the direct or indirect product/s of the amplification reaction), it may be desirable to alter the profile of the thermal shuttling during the course of the reaction, so that not all of the shuttles are identical. More specifically, if real-time quantification of the amplification reaction product/s (whether direct or indirect) indicates that the reaction is proceeding more slowly than is desirable, this information might be fed back to the thermal regulation apparatus which regulates the temperature of the reaction mixture, causing the apparatus to adjust the profile of the thermal shuttling, so as to increase the rate of reaction. This might be required if, for example, the target sequence is present in very low copy number. The apparatus might adjust the thermal shuttling profile by increasing or decreasing the upper and/or lower temperature, and/or increasing or decreasing the dwell time at the upper and/or lower temperature. It is also feasible that the apparatus might increase or decrease the time taken to transition between the upper and lower temperatures (i.e. increase or decrease the time of either the upward temperature transition, or the downward temperature transition, or both).

The thermal shuttling may be commenced substantially immediately after all the necessary components of the reaction mixture have been brought together.

Alternatively, the thermal shuttling may be commenced after a delay interval. For example, it is possible, and potentially desirable, that the reaction mixture might be held at an elevated temperature (which might be the same as, or different to, the upper temperature used in the thermal shuttling). As an illustration, such a delay interval might be from e.g. 5 seconds to 1 or 2 minutes.

Further, the thermal shuttling may conveniently be performed substantially continuously during the amplification reaction, or may be subject to one or more pauses. Typically, and preferably, once commenced the thermal shuttling will not be interrupted until the amplification reaction has reached a desired time point, typically by when a detectable fluorescence (or other) signal has been obtained and which allows advantageously quantitative determination of the amount and/or concentration of the target sequence in the sample.

The thermal shuttling of the amplification reaction mixture may conveniently be effected using automated thermal regulation apparatus, such as is commercially available for performing thermal cycling in PCR. Clearly the temperature profiles generated by the apparatus will need matching to the preferred conditions applicable in performance of the present invention.

In a second aspect, the invention provides a reaction mixture for performing a nucleic acid amplification, the mixture comprising a target sequence to be amplified, two or more primers, one of said primers being complementary to a first strand of the target and the other of said primers being complementary to a second strand of the target, a DNA polymerase, and a nicking enzyme; said reaction mixture being in thermal regulation association with programmable temperature regulation means, said temperature regulation means being programmed to perform thermal shuttling between an upper and lower temperature, as defined previously in relation to the first aspect of the invention.

In a third aspect, the invention provides a method of determining the amount and/or concentration of a target polynucleotide in a sample, the method comprising the steps of: performing an amplification reaction in accordance with the first aspect of the invention defined above to amplify the target and detecting, in a quantitative manner, the direct or indirect product/s of the amplification reaction, so as to allow a determination of the amount and/or concentration of the target polynucleotide in the sample.

The amplification process of the method of the invention may be applied to generally known and conventional amplification techniques including SDA and NEAR, which utilise a polymerase and a nicking enzyme. Thus, for example, the amplification process may be based on the amplification process employed in strand displacement amplification, or based on that used in NEAR or indeed any other nucleic acid amplification process which relies on the creation of a single stranded nick and subsequent extension from the 3' end of the nicked strand. Other than the teachings of the prior art in relation to maintenance of constant temperature during the amplification, the teachings of the prior art in relation to the amplification stages of SDA or NEAR will, in general, be equally applicable to the amplification process of the method of the present invention.

The method of the present invention is an improvement of the amplification technique named Selective Temperature Amplification Reaction (or "STAR") described in WO2018/002649. The method of the present invention, in preferred embodiments, permits real-time quantitative detection of target sequences, and is referred to herein as "qSTAR", although this is not intended to indicate that the method of the invention will provide quantitative real-time results under all conditions.

Preferably step (a) comprises mixing a sample containing double stranded target with two single stranded primers, one of said primers being complementary to a first strand of the target, and the other of said primers being complementary to a second strand of the target, such that the two primers hybridise to the target and the free 3' ends of said primers face towards one another.

The two primers may conveniently be described as 'forward' and 'reverse' primers.

Desirably both the forward and reverse primers will comprise the sequence of a nicking enzyme recognition site. Typically the nick created by a nicking enzyme will be just outside and typically 3' of the nicking enzyme recognition site.

In a preferred embodiment, the forward primer will comprise a portion at or near its 3' end which is complementary to, and can hybridise with, the 3' end of the target sequence antisense strand, whilst the reverse primer comprises a portion at or near its 3' end which is complementary to, and can hybridise with, the 3' end of the target sequence sense strand.

In this way, a nicking enzyme recognition site is introduced at opposite ends of the target sequence, and amplification of the target sequence (together with any intervening sequence of the primers downstream of the nick site) is accomplished by performing multiple cycles of polymerase extension of the forward and reverse primers so as to form a double stranded nicking enzyme recognition site, and by nicking of the sites with a nicking enzyme, allowing further extension of the nicked primers by a polymerase etc., essentially as disclosed in, for example, US 2009/0017453, the content of which is herein incorporated by reference.

The target may be single stranded, double stranded, or comprise a mixture of the two. The target may comprise RNA, DNA or a mixture of the two. In particular the target might incorporate one or more modified nucleotide triphosphates (i.e. a nucleotide triphosphate not normally found in naturally occurring nucleic acids), although this is not essential and indeed not preferred.

The target may be selected from the following non-exhaustive list: genomic nucleic acid (which term encompasses the genomic nucleic acid of any animal, plant, fungus, bacterium or virus), plasmid DNA, mitochondrial DNA, cDNA, mRNA, rRNA, tRNA, or a synthetic oligonucleotide or other nucleic acid molecule.

In particular, the method may additionally comprise an initial reverse transcription step. For example, RNA (e.g. viral genomic RNA, or cellular mRNA, or RNA from some other source) may be used to synthesise DNA or cDNA using a reverse transcriptase by methods well-known to those skilled in the art. The DNA may then be used as a target sequence in the method of the invention. The original RNA will typically be degraded by the ribonuclease activity of reverse transcriptase, but if desired additional RNase H may be added after reverse transcription has been completed. RNA molecules are often present in samples at greater copy number than corresponding (e.g. genomic) DNA sequences, hence it may be convenient to make DNA transcripts from the RNA molecule in order to effectively increase the copy number of the DNA sequence.

The "target sequence" is the sequence of bases in the target nucleic acid, and may refer to the sense and/or antisense strand of a double stranded target, and also encompasses, unless the context dictates otherwise, the same base sequence as reproduced or replicated in amplified copies, extension products or amplification products of the initial target nucleic acid.

The target sequence may be present in any kind of sample e.g. biological or environmental (water, air etc.). A biological sample may be, for example, a food sample or a clinical sample. Clinical samples may include the following: urine, saliva, blood, serum, plasma, mucus, sputum, lachrymal fluid or faeces.

The sample may or may not be subject to processing before being contacted with the primers. Such processing may include one or more of: filtration, concentration, partial-purification, sonication, chemical lysis and the like. Such processes are well-known to those skilled in the art.

The method of the present invention involves the use of a nick site and means for creating a nick at the nick site. A "nick" is the cleavage of the phosphodiester backbone of just one strand of a fully, or at least partially, double stranded nucleic acid molecule. The nick site is the location in the molecule where a nick is made.

In preferred embodiments a "nicking recognition site" will be present at, within, or next to a nick site. ("Next to" in this context means that the nearest base of the nicking recognition site is within 10 bases of the nick site, preferably within 5 bases of the nick site).

The nicking recognition site may comprise at least one strand of the recognition site of a restriction endonuclease, and the nick site may comprise at least one strand of a nucleic acid base sequence which, when present as a double stranded molecule, is cut by a restriction endonuclease. Typically a restriction endonuclease will cut both strands of a double stranded nucleic acid molecule. In the present invention, a double stranded break can be avoided by the incorporation of one or more modified bases at or near to the nick site, which modified bases render a strand of nucleic acid not susceptible to cleavage by the restriction endonuclease. In this way a restriction endonuclease, which usually cuts both strands of a double stranded nucleic acid molecule, can be used to introduce a single stranded nick into a double stranded molecule. Modified bases and the like suitable for achieving this are well-known to those skilled in the art and include, for example, all alpha phosphate modified nucleoside triphosphates and alpha borano modified nucleoside triphosphates, specifically; 2'-deoxyadenosine 5'-O-(thiotriphosphate), 5-methyldeoxycytidine 5'-triphosphate, 2'-deoxyuridine 5'triphosphate, 7-deaza-2'deoxyguanosine 5'-triphosphate, 2'deoxyguanosine-5'-O-(1-boranotriphosphate) and others. Triphosphates including the modified base may be present within a reaction mixture used to perform the amplification process, so that modified bases are incorporated at relevant positions during subsequent rounds of amplification to prevent the formation of a double-stranded site cleavable by the endonuclease.

In preferred embodiments however the nick is made at the nick site by means of a nicking enzyme. Nicking enzymes are molecules which, under normal circumstances, make only a single stranded break in a double stranded nucleic acid molecule. The nicking enzyme typically has a nicking recognition site and the nick site may be within the nicking recognition site or may be either 5' or 3' of the recognition site. Many nicking enzymes are known to those skilled in the art and are commercially available. A non-exhaustive list of examples of nicking enzymes includes: Nb.Bsml, Nb.Bts, Nt.Alwl, Nt.BbvC, Nt.BstNBI, and Nt.Bpu101. The latter enzyme is commercially available from ThermoFisher Scientific; the others are available from e.g. New England Biolabs.

In preferred embodiments, the nicking enzyme is introduced into the reaction mixture at the outset of the method (e.g. within one minute of contacting the sample with primers and DNA polymerase). However, in some instances it may be desirable to introduce the nicking enzyme into the reaction mixture after a longer delay (e.g. to allow the temperature to fall closer to the optimum temperature of the nicking enzyme).

The method of the invention involves the use of a DNA polymerase. Preferably, but not necessarily, the method of the invention may comprise the use of at least one thermophilic DNA polymerase (i.e. having an optimum temperature in excess of 60° C.). Preferably the DNA polymerase is a strand displacing polymerase. Preferably the DNA polymerase has no exonuclease activity. Preferably the DNA polymerase is a strand-displacing, polymerase with no exonuclease activity, and is also preferably thermophilic.

Examples of preferred DNA polymerases include Bst polymerase, VENT® DNA polymerase, 9° N polymerase, MANTA™ 1.0 polymerase (Qiagen), BstX polymerase (Qiagen), SD polymerase (Bioron GmbH), Bsm DNA polymerase, large fragment (ThermoFisher Scientific), Bsu DNA polymerase, large fragment (NEB), and "ISOPOL"™ polymerase (from ArcticZymes).

The table below gives examples of combinations of a nicking enzyme and a DNA polymerase, together with the suggested upper and lower temperature to use in performing the method of the invention using the exemplified enzyme combinations. Although the table lists specific DNA polymerases, these are by way of example only and any strand displacing exonuclease minus, polymerase with activity in the stated temperature range would suffice such as: DEEP VENT™ (exo-), Bst DNA Polymerase I, II, and Ill, MANTA™ 1.0 DNA Polymerase, Bst X DNA Polymerase, Bsm DNA Polymerase, ISOPOL™ DNA Polymerase.

| Suggested Nicking Enzyme(s) | Suggested DNA Polymerase(s) | Suggested Upper Temperature (° C.) | Suggested Lower Temperature (° C.) |
| --- | --- | --- | --- |
| Nt.BstNBI | Bst DNA Polymerase, Large Fragment | 62° C. | 57° C. |
| Nt.BstNBI | Bsu DNA Polymerase, Large Fragment | 45° C. | 38° C. |
| Nt.Alwl | Bst DNA Polymerase, Large Fragment | 62° C. | 57° C. |
| Nt.Alwl | Bsu DNA Polymerase, Large Fragment | 45° C. | 38° C. |
| Nt.BsmAl | Bst DNA Polyerase, Large Fragment | 60° C. | 55° C. |
| Nt.BsmAl | Bsu DNA Polymerase, Large Fragment | 44° C. | 37° C. |
| Nt.BspQ1 | Bst DNA Polymerase, Large Fragment | 62° C. | 52° C. |
| Nt. BspQ1 | Bsu DNA Polymerase, Large Fragment | 44° C. | 37° C. |

In some embodiments, the method of the invention may conveniently comprise a pre-amplification or enrichment step. This is a step in which the target sequence is contacted with forward and reverse primers and DNA polymerase, but no nicking enzyme. This typically lasts for about 1-5 minutes and produces an initial (linear) amplification of the target sequence of about 1,000 fold, which can be especially useful if the target sequence is present in the sample at low copy number.

In some embodiments, the pre-amplification or enrichment step is performed using a mesophilic DNA polymerase such as Exo-Minus Klenow DNA Polymerase or Exo-Minus psychrophile DNA polymerase from Cenarchaeum symbiosum, at a temperature below 50° C., and the mixture is subsequently heated above 50° C. to denature or inactivate the thermolabile DNA polymerase, and then a thermophilic DNA polymerase is added for downstream amplification.

Typically, the method of the invention comprises a detection step, in which one or more of the direct or indirect products of the amplification process is detected and optionally quantified, this indicating the presence and/or amount of the target in the sample. There are a great many suitable detection and/or quantification techniques known, including: gel electrophoresis, mass spectrometry, lateral flow capture, incorporation of labelled nucleotides, intercalating or other fluorescent dyes, enzyme labels, electrochemical detection techniques, molecular beacons and other probes, especially specifically hybridising oligonucleotides or other nucleic acid containing molecules.

The product or products which are detected in the detection step may be referred to herein as the "detection target". The 'target' in relation to the detection step, is not necessarily the same as the 'target' in the amplification process and indeed the two molecules will usually be different to at least some extent, although they may have some sequence (typically 10-20 bases) in common, where the detection target comprises a nucleic acid molecule or oligonucleotide.

Nucleic acid detection methods may employ the use of dyes that allow for the specific detection of double-stranded DNA. Intercalating dyes that exhibit enhance fluorescence upon binding to DNA or RNA are well known. Dyes may be, for example, DNA or RNA intercalating fluorophores and may include inter alia the following: acridine orange, ethidium bromide, Pico Green, propidium iodide, SYBR® I, SYBR® II, SYBR® Gold, TOTO-3 (a thiaxole orange dimer) OLIGREEN™ and YOYO™ (an oxazole yellow dimer).

Nucleic acid detection methods may also employ the use of labelled nucleotides incorporated directly into the detection target sequence or into probes containing sequences complementary or substantially complementary to the detection target of interest. Suitable labels may be radioactive and/or fluorescent and can be resolved in any of the manners conventional in the art. Labelled nucleotides, which can be detected but otherwise function as native nucleotides (e.g. are recognised by and may act as substrates for, natural enzymes), are to be distinguished from modified nucleotides, which do not function as native nucleotides.

The presence and/or amount of target nucleic acids and nucleic acid sequences may be detected and monitored using molecular beacons. Molecular beacons are hair-pin shaped oligonucleotides containing a fluorophore at one end and a quenching dye ("quencher") at the opposite end. The loop of the hair-pin contains a probe sequence that is complementary or substantially complementary to a detection target sequence and the stem is formed by the annealing of self-complementary or substantially self-complementary sequences located either side of the probe sequence.

The fluorophore and the quencher are bound at opposite ends of the beacon. Under conditions that prevent the molecular beacon from hybridizing to its target or when the molecular beacon is free in solution, the fluorophore and quencher are proximal to one another, preventing fluorescence. When the molecular beacon encounters a detection target molecule, hybridization occurs; the loop structure is converted to a stable, more rigid conformation causing separation of the fluorophore and quencher allowing fluorescence to occur (Tyagi et al. 1996, Nature Biotechnology 14: 303-308). Due to the specificity of the probe, the generation of fluorescence is substantially exclusively due to the presence of the intended amplified product/detection target.

As a general rule, molecular beacons work better at lower hybridisation temperatures, as the signal to noise ratio decreases with increasing temperature. This is because at lower temperatures the self-complementary "stem" parts of the molecular beacon remain firmly hybridised, allowing the quencher to quench the fluorophore, but as the temperature increases the stem parts of the molecule can start to melt, allowing non-specific fluorescence background "noise" to increase.

Molecular beacons are highly specific and can distinguish nucleic acid sequences differing by a single base (e.g. single nucleotide polymorphisms). Molecular beacons can be synthesized with different coloured fluorophores and different detection target complementary sequences, enabling several different detection targets in the same reaction to be detected and/or quantified simultaneously, allowing "multiplexing" of a single PoC assay to detect a plurality of different pathogens or biochemical markers. For quantitative amplification processes, molecular beacons can specifically bind to the amplified detection target following amplification, and because non-hybridized molecular beacons do not fluoresce, it is not necessary to isolate probe-target hybrids to quantitatively determine the amount of amplified product. The resulting signal is proportional to the amount of the amplified product. This can be done in real time. As with other real time formats, the specific reaction conditions must be optimized for each primer/probe set to ensure accuracy and precision.

The production or presence of detection target nucleic acids and nucleic acid sequences may also be detected and monitored by fluorescence resonance energy transfer (FRET). FRET is an energy transfer mechanism between two fluorophores: a donor and an acceptor molecule. Briefly, a donor fluorophore molecule is excited at a specific excitation wavelength. The subsequent emission from the donor molecule as it returns to its ground state may transfer excitation energy to the acceptor molecule (through a long range dipole-dipole interaction). FRET is a useful tool to quantify molecular dynamics, for example, in DNA-DNA interactions as seen with molecular beacons. For monitoring the production of a specific product a probe can be labelled with a donor molecule on one end and an acceptor molecule on the other. Probe-detection target hybridization brings a change in the distance or orientation of the donor and acceptor and a change in the FRET properties is observed. (Joseph R. Lakowicz. "Principles of Fluorescent Spectroscopy", Plenum Publishing Corporation, $2^{nd}$ edition (Jul. 1, 1999)).

The production or presence of detection target nucleic acids may also be detected and monitored by lateral flow devices. Lateral Flow devices are well known. These devices generally include a solid phase fluid permeable flow path through which fluid flows by capillary force. Examples include, but are not limited to, dipstick assays and thin layer chromatographic plates with various appropriate coatings. Immobilized in or on the flow path are various binding reagents for the sample, binding partners or conjugates involving binding partners for the sample, and signal producing systems. Detection of analytes can be achieved in several different ways including: enzymatic detection, electrochemical detection, nano-particle detection, colorimetric detection, and fluorescence detection. Enzymatic detection may involve enzyme-labelled probes that are hybridized to complementary or substantially complementary nucleic acid detection targets on the surface of the lateral flow device. The resulting complex can be treated with appropriate markers to develop a readable signal. Nanoparticle detection involves bead technology that may use colloidal gold, latex and paramagnetic nanoparticles. In one example, beads may be conjugated to an anti-biotin antibody. Target sequences may be directly biotinylated, or target sequences may be hybridized to a sequence specific biotinylated probes. Gold and latex give rise to colorimetric signals visible to the naked eye and paramagnetic particles give rise to a non-visual signal when excited in a magnetic field and can be interpreted by a specialized reader.

Fluorescence-based lateral flow detection methods are also known, for example, dual fluorescein and biotin-labelled oligo probe methods, or the use of quantum dots.

Nucleic acids can also be captured on lateral flow devices. Means of capture may include antibody dependent and antibody independent methods. Antibody-independent capture generally uses non-covalent interactions between two binding partners, for example, the high affinity and irreversible linkage between a biotinylated probe and a streptavidin capture molecule. Capture probes may be immobilised directly on lateral flow membranes.

The entire method of the invention, or at least the amplification process portion of the method, may be performed in a reaction vessel (such as a conventional laboratory plastics reagent tube e.g. from Eppendorf®) or may be performed in and/or on a solid support. The solid support may be porous or non-porous. In a particular embodiment the solid support may comprise a porous membrane material (such as nitrocellulose or the like). More especially the solid support may comprise or form part of a porous lateral flow assay device, as described above. Alternatively, the solid support may comprise or form part of a microfluidics-type assay, in which one or more solid narrow-bore capillary tubes are used to transport a liquid along an assay device.

In preferred embodiments, all or at least part of the method of the invention may be performed using a point-of-care (PoC) assay device. A PoC device typically has the following characteristics: it is cheap to manufacture, is disposed of after a single use, is generally self-contained not requiring any other apparatus or equipment to perform or interpret the assay and, desirably, requires no clinical knowledge or training to use.

The method of the invention especially lends itself to performance using a PoC-type device since, in typical embodiments, the difference in temperature between the upper and lower temperatures of the thermal shuttle is quite small. As a result, relatively simple thermal shuttling/temperature regulation is sufficient, in contrast say, to performing qPCR.

Nevertheless, the amplification method of the present invention could also be used in a lab-based system, rather than a PoC device, in place of qPCR and can typically achieve quantitative results much more quickly than can be achieved by performing qPCR.

Examples of primers suitable for use in the invention are disclosed herein. Other examples which may be suitable for use in the method of the invention are disclosed in, inter alia, US 2009/0017453, US2013/0330777, and EP 2,181,196, the content of which is incorporated herein by reference. The person skilled in the art will be readily able to design other primers suitable for the amplification of other target sequences without undue experimentation.

As explained elsewhere, primers of use in the invention will preferably comprise not only a target complementary portion, but also a nicking endonuclease binding site and nicking site, and a stabilizing portion.

Primers of use in the method of the invention may comprise modified nucleotides (i.e. nucleotides not found in naturally occurring nucleic acid molecules). Such modified nucleotides may conveniently be present in the target complementary portion of the primer, and/or elsewhere in the primer. Preferred examples of modified nucleotides are 2'-modified nucleotides, especially 2'-O-methyl modified nucleotides, although many other modified nucleotides are known to those skilled in the art.

BRIEF DESCRIPTION OF THE DRAWINGS

The features of the invention will now be described by way of illustrative example and with reference to the accompanying drawings, in which:

FIGS. 4, 5A, 5B and 5C are graphs of (background subtracted) fluorescence (in arbitrary units) against time (seconds) for amplification reactions performed in accordance with the method of the invention, using primer molecules comprising no 2'-O-methylated bases (FIG. 4), or primer molecules comprising one, six, or seven 2'-O-methylated bases (FIGS. 5A, 5B and 5C respectively);

FIGS. 10A-11D are graphs of relative fluorescence (arbitrary units) against cycle number for amplification reactions attempted using various different polymerase enzymes using conventional PCR conditions (FIGS. 10A, 10B) or "qSTAR" thermal shuttling conditions in accordance with the invention but in the absence of a nicking enzyme (FIGS. 11A-11D);

FIGS. 12, and 13A and 13B show the data obtained from performing conventional qPCR amplification (FIG. 12), or "qSTAR" amplification in accordance with the method of the invention (FIG. 13A), using starting samples of unknown concentration, with a summary of the results in FIG. 13B;

EXAMPLES

Example 1: Protocol for Testing Quantitative Selective Temperature Amplification Reaction (qSTAR)

Quantifying gene expression by Selective Temperature Amplification Reaction (STAR) as described in WO2018/002649, or other similarly related DNA/RNA amplification technologies such as PCR, SDA, or an isothermal amplification technique, would be, at best, unreliable. The amount of product produced would reach a plateau that is not directly correlated with the amount of target DNA in the initial starting sample. By establishing a zonal effect of controlled temperature shuttling on an amplification reaction, quantitative amplifications can be achieved with a strand displacement polymerase and nicking endonuclease in which the amplified product is directly related to the initial starting amount of DNA, RNA, or other known nucleic acids. A nicking enzyme-based selective temperature amplification reaction, in accordance with the invention, is referred to herein as quantitative Selective Temperature Amplification Reaction (qSTAR). The protocol is further described below unless otherwise noted.

Enzymes, Oligonucleotides, and Target

*Chlamydia trachomatis* (Ct) was used as the initial target for the development of the qSTAR mechanism. *Chlamydia trachomatis* Serovar J (ATCC VR-886) genomic DNA was acquired from American Type Culture Collection (Manassas, Va.). The open reading frame 6 region of the cryptic plasmid was amplified with primers qSTARctF61a (SEQ ID NO: 15'-CGACTCCATATGGAGTCGATTTCCCCG AATTA-3') and qSTARctR61c (SEQ ID NO: 2 5'-GGACTCCACACGGAGTCTTTTTCCTTGTTTAC-3'). The resulting DNA template was detected using a molecular beacon qSTARctMB1 (SEQ ID NO: 3, 5'-FAM/ccat-tCCTTGTTTACTCGTATTTTTAGGaatgg/BHQ1-3') as described in EP No. 0728218. Bst X DNA polymerase was purchased from Qiagen (Beverly, Mass.). Nt.BstNBI nicking endonuclease was purchased from New England Bio-Labs (Ipswich, Mass.) and is described in U.S. Pat. No. 6,191,267. The same polymerase and nicking endonuclease were also used in the other examples described herein, unless otherwise stated.

Oligonucleotides and molecular beacons were synthesized by Integrated DNA Technologies (Coralville, Iowa) and Bio-Synthesis (Lewisville, Tex.). The general features of the primers used in the qSTAR reactions are as described in WO2018/002649.

Figure 1A:
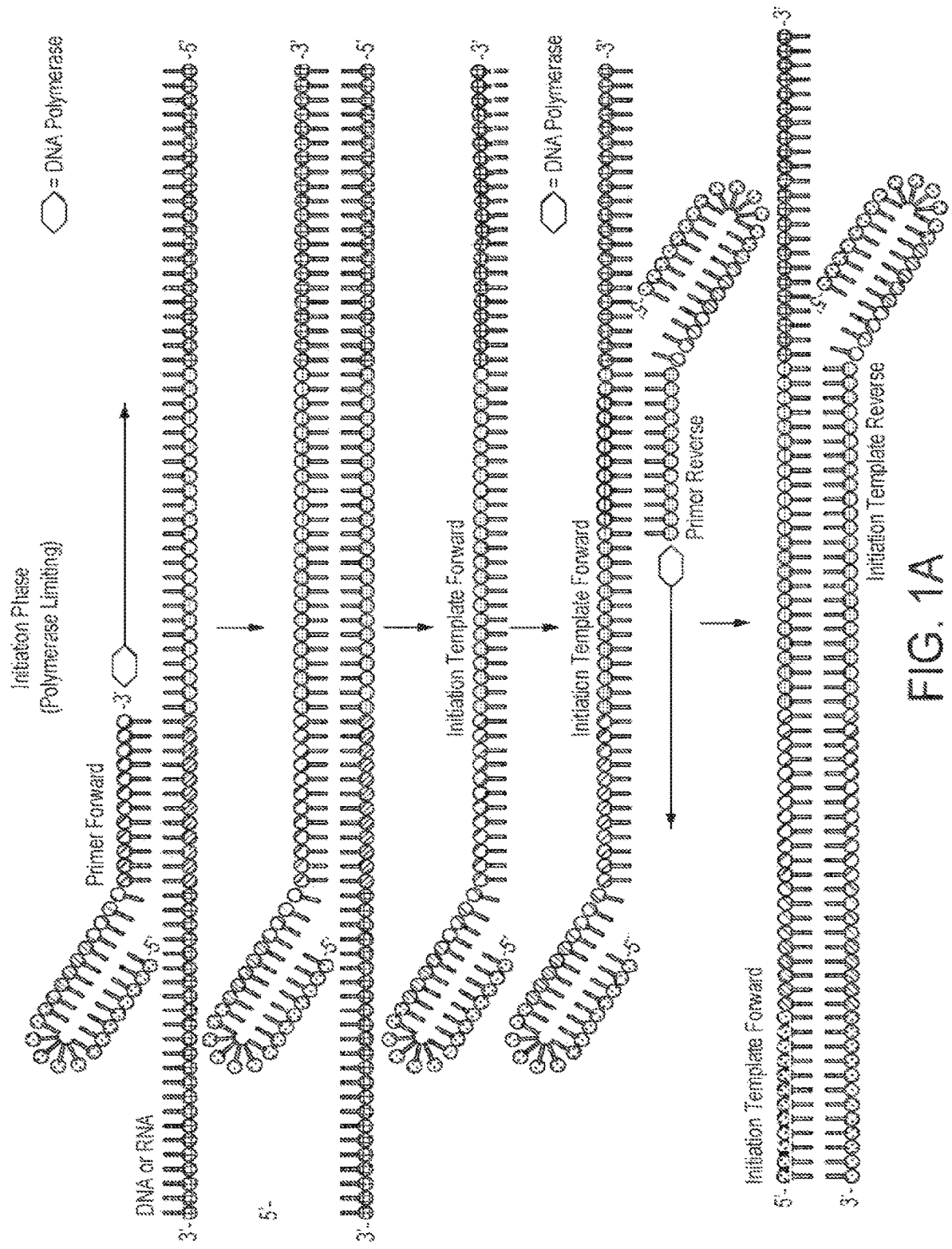
FIGS. 1A and 1B are schematic representations of the initiation phase and exponential amplification phase respectively of a nucleic acid amplification reaction suitable for performing the method of the invention.

A summary of the oligonucleotides and amplification mechanism found in a reaction in one embodiment of the present invention comprises (i) a target nucleic acid molecule; (ii) two or more primer oligonucleotide molecules comprising some number of oligonucleotides that are complementary to the target nucleic acid molecule and (iii) a site within the primer that can be nicked by a nicking enzyme. The method involves contacting a target nucleic acid molecule with a polymerase, two or more primer oligonucleotides, each of which specifically binds to a complementary sequence on the target nucleotide molecule, and a nicking enzyme, under selective temperature amplification conditions, generating a detectable amplicon that comprises at least a portion of the target sequences that a primer oligonucleotide had bound to. The overall qSTAR reaction can be understood to undergo two distinct phases; initiation and exponential amplification, illustrated schematically in FIGS. 1A and 1B respectively. The initiation phase is the initial formation of a protein-primer duplex from which initial extension for exponential amplification can occur. The exponential phase is when the nicking enzyme becomes active along with the polymerase leading to exponential amplification. In FIG. 1A, initial contact of the primer to a target nucleic acid occurs (step a), followed by polymerase extension (step b) which generates the forward initiation template (c). The opposite strand primer binds (step d) to the newly generated forward initiation template, extending (step e) in the direction toward, and through, the initiation template's nick site. This initiation can occur simultaneously on both the forward and reverse strands. This initial process can be understood as predominantly involving the polymerase for extension, but with essentially little or no involvement of the nicking enzyme.

In FIG. 1A, the target is shown as being single stranded. This is for the purposes of clarity and simplicity. In reality, the method of the invention is performed without requiring the use of high temperatures to 'melt' or separate the strands of double stranded target polynucleotides—rather, primers are able to associate with the (double stranded) target molecule by taking advantage of localised relaxation of the hydrogen bonding between the strands—a phenomenon known as "breathing".

Figure 1B:
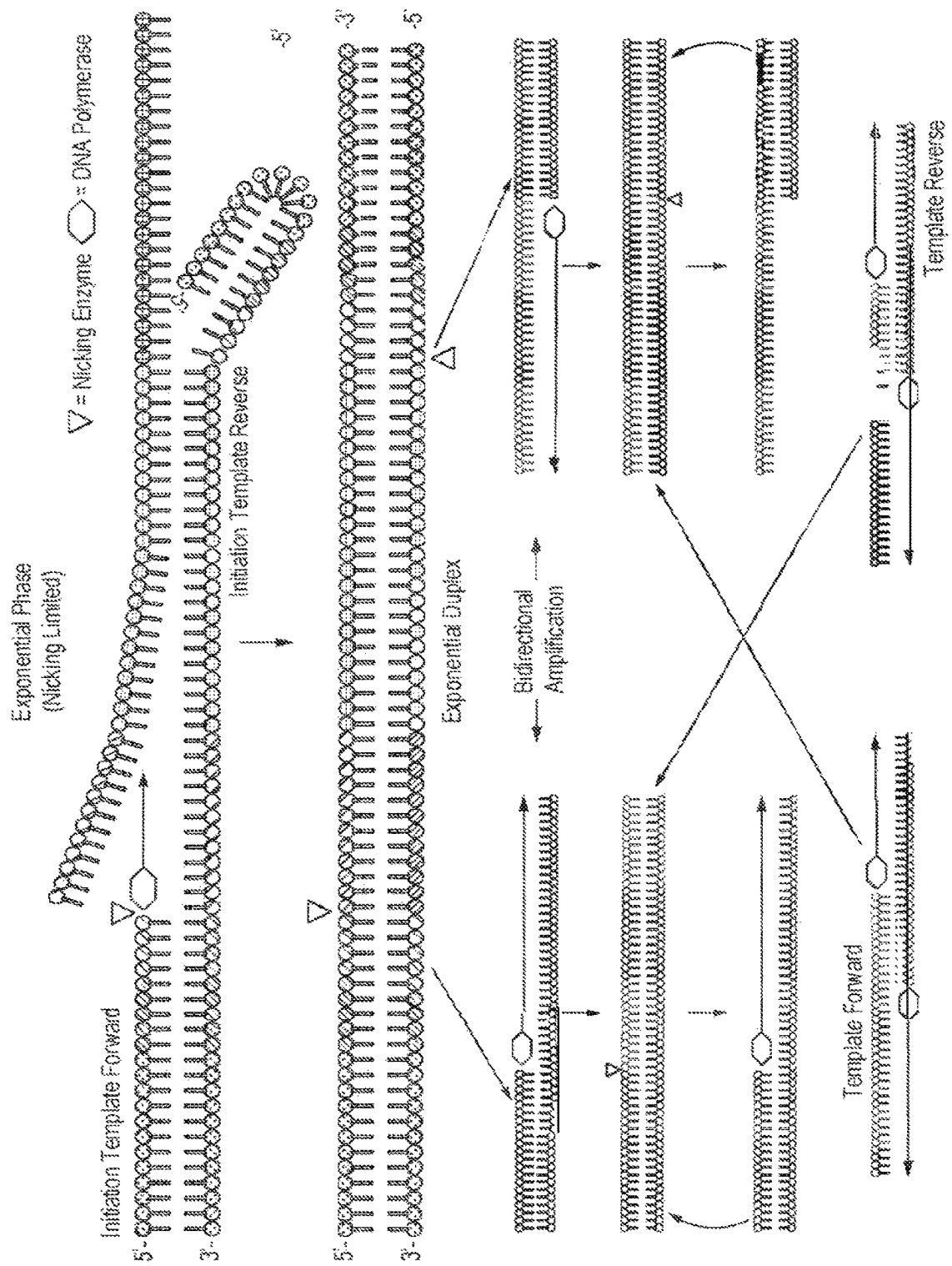

At a (in this embodiment, lower) second selective temperature, nicking is favoured on either strand allowing the strand displacing polymerase to extend toward the opposite primer and through the nick site. This cycle of nicking/polymerase extension results in the formation of the Exponential Duplex (FIG. 1B). This Exponential Duplex then feeds into a bidirectional amplification as each new template generated from a nick and extension becomes a target for another primer. The temperature is shuttled back to the initiation phase for polymerase specific extension, limiting background amplification and controlling exponential amplification in discreet phases.

By controlling the temperatures, and thus the activity of the polymerase and nicking endonuclease, the applicants have achieved a method for rapid and controlled amplification, allowing for quantitation of unknown target input.

Figure 2:
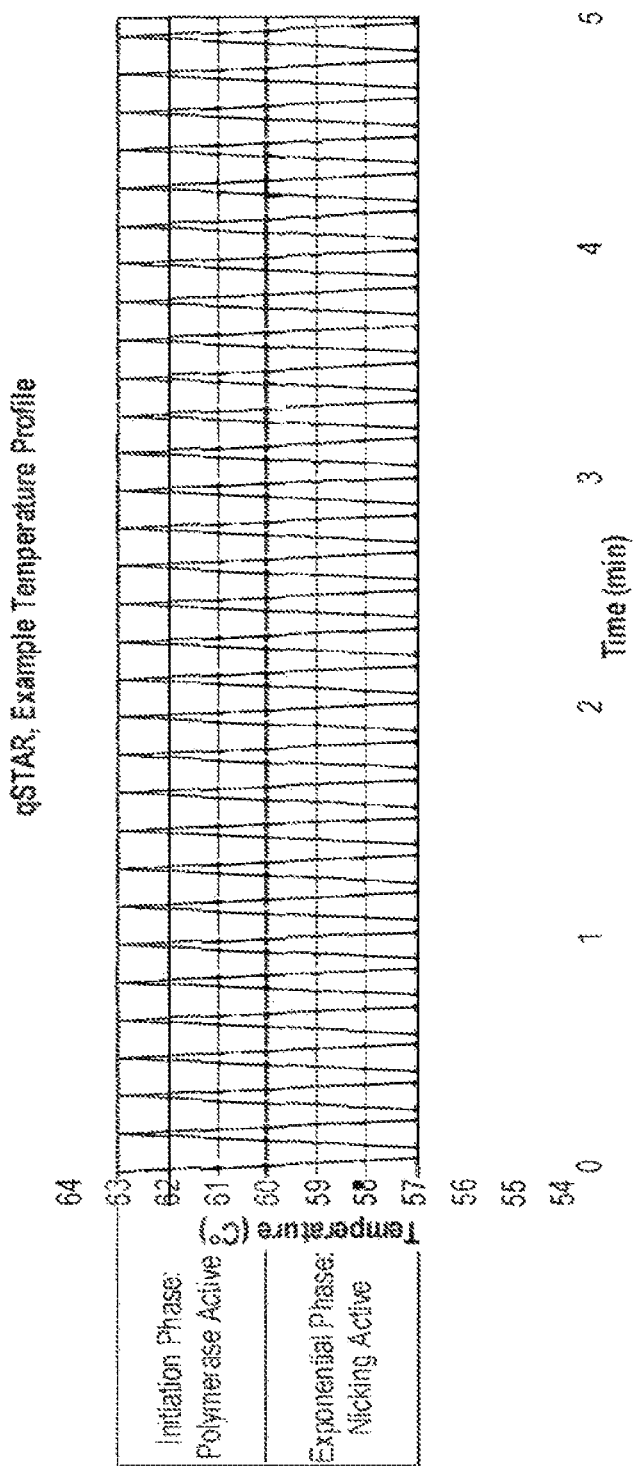
FIG. 2 is a graph (temperature in ° C. against time, in minutes) illustrating a typical temperature profile for a reaction mixture during performance of the method of the invention.

FIG. 2 shows a typical temperature profile (° C. against time, in minutes) for one embodiment of a amplification reaction in accordance with the invention. In the illustrated embodiment, the polymerase has a higher optimum temperature than that of the nicking enzyme. The upper temperature is 63° C., the lower temperature is 57° C. The dwell time at the lower temperature (about 5 seconds) is longer than the dwell time (about 2 seconds) at the upper temperature. Each complete temperature shuttle lasts about 8-9 seconds, such that approximately 7 thermal shuttles are completed per minute. In the upper temperature half of the shuttle (>60° C.) the initiation phase of the reaction (see FIG. 1B) is favoured and predominates. Those skilled in the art will appreciate that there is no sharp temperature distinction between the two phases of the amplification reaction, and the dividing line illustrated in FIG. 2 is simply to aid understanding.

The approach of quantitative selective temperature amplification has surprisingly resulted in a quantitative, rapid, specific, and high yield amplification reaction with significantly greater performance than previously existing methods, as will be further explained and illustrated in greater detail below.

Amplification Conditions

The basic qSTAR mixture contained two primers, polymerase, and nicking enzyme (referenced above). The reactions were performed in a final volume of 25 µl, including 1.0 µM of the forward primer, 0.5 µM of the reverse primer, 0.25 µM molecular beacon, 10 µl qSTAR Master Mix and 5 µl DNA sample. qSTAR master mix contained the following reagents; 12.5 mM $MgSO_4$, 90 mM Tris-HCl (pH 8.5), 300 µM each dNTPs, 20 mM $NH_4OAc$, 30 mM NaOAc, 2 mM DTT, 0.02% TRITON® X-100, 15U nicking endonuclease and 60 U polymerase. The temperature of the reactions was controlled between two discreet temperature phases to take advantage of inherent enzyme activities. The initiation phase, consisting primarily of polymerase activity, was at the elevated temperature of 62° C. for two seconds. (At this temperature the nicking enzyme was largely inhibited—see FIG. 9B). The exponential phase, in which both the polymerase and nicking enzyme are moderately or highly active, was held at 57° C. for five seconds. The total time for a complete shuttle was 15 seconds. This is more than double the dwell time at each temperature due to the limits of the apparatus in changing temperature (a more responsive instrument would allow for faster shuttling between upper and lower temperature). Amplification and qSTAR product detection were performed using the Agilent Mx3005P qPCR apparatus (Agilent).

Every reaction had a pre-incubation to allow the reagents to come to reaction temperature and to test the effect that temperature had on amplification kinetics, enzyme performance, and signal fluorescence.

Amplification Procedure

The exact steps under which an amplification reaction was performed are as follows: 1) prepare master mix; 2) prepare primers with target or no target; 3) add primer mixes to rows A-G of a 96 well plate, depending on number of reactions to be done per plate; 4) add master mix to row H of the same 96 well plate; 5) seal plate and do a pre-reaction incubation for 15 seconds; 6) transfer master mix from row H to each primer mix row; 7) seal and initiate preselected temperature profile and data collection.

During the reaction, amplified product was measured at the end of every exponential phase using a molecular beacon as described below. The fluorescence of the molecular beacon in the reaction mixture was monitored to measure the amount of specific product being generated during a reaction which binds to the molecular beacon separating the fluorophore from the quencher, generating fluorescence.

Example 2: Results Using Unmodified Primers

Figure 4:
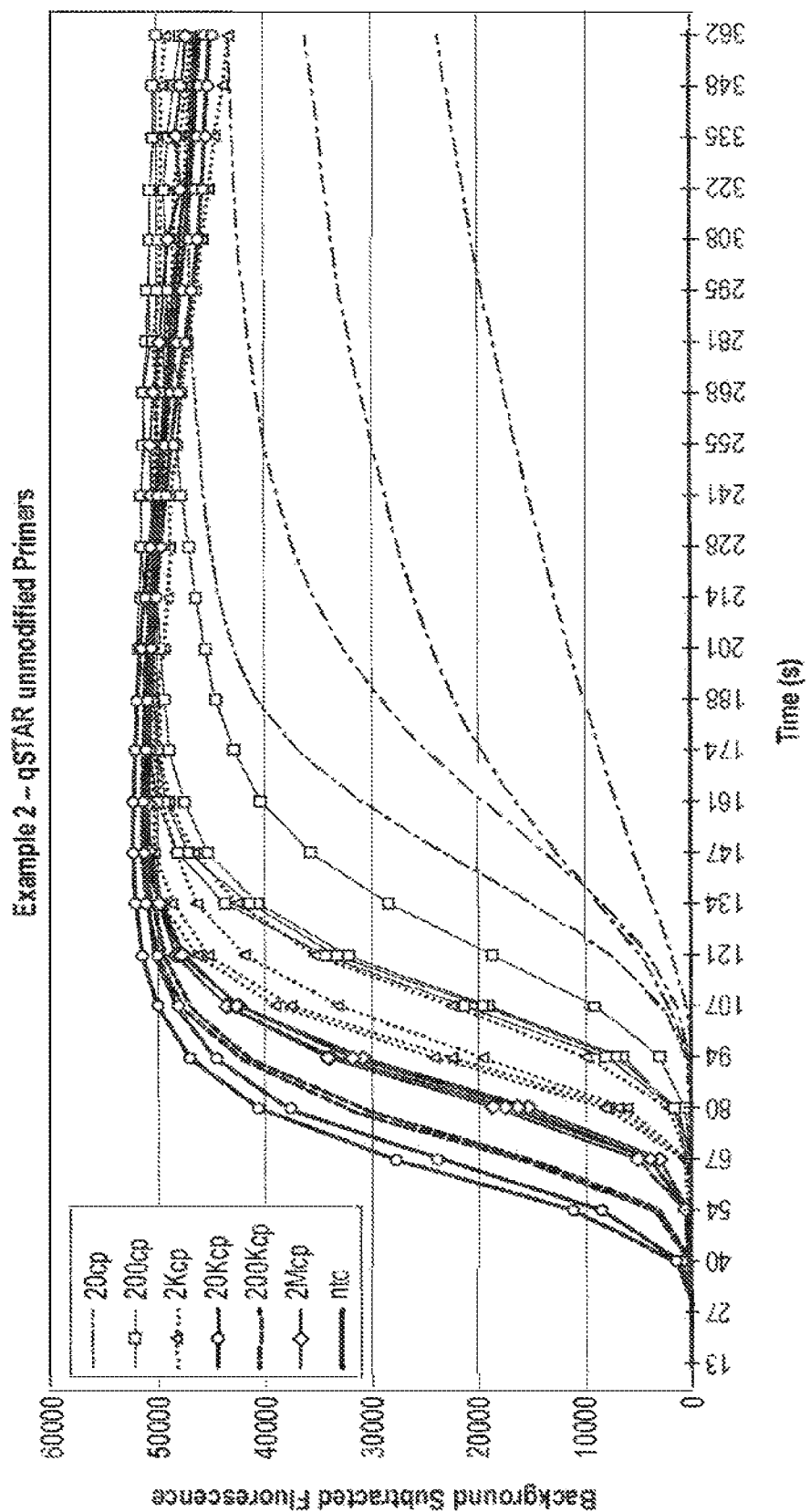

To demonstrate the potential of this novel amplification technology, qSTAR was carried out using four replicates per target dilution across 6-logs of genomic DNA input, and two replicates for no target controls (NTC). The results of experiments using unmodified primers (i.e. primer molecules not containing any chemically-modified, abnormal nucleic acid bases) are shown in FIG. 4. The amount of signal (background subtracted fluorescence) for the "no-target control" is indicated by the dark line ("ntc"). The amount of signal generated in the presence of 20 cp, 200 cp, 2 k, 20 k, 200 k, and 2M copies of target (genomic DNA of C. trachomatis) is indicated by the respective lines.

The qSTAR reactions display a linear coefficient of determination from the target input while also demonstrating an improvement in speed, sensitivity, and total fluorescence. It is surprising and unexpected that such an improvement and separation between target inputs could be achieved by controlling the temperature of the reactions between two close but distinctly different, temperature regions.

Without limiting the inventors to any particular theory, it is believed that the amplification improvements can be attributed to at least two characteristics. In most nucleic acid amplification reactions, primer dimers eventually form, competing for limited reagents and, at low target concentrations, primer dimers may potentially become the primary amplification pathway for a reaction. Limiting or delaying the formation of primer dimers, even by a small amount, provides significant benefits. Because of the rapid nature of the amplification reaction, delaying primer-dimer formation allows for preferred amplification pathways to be favoured (i.e. template generation) improving all aspects of amplification. By initiating reactions at elevated temperatures these template pathways become favoured and even preferred. This is seen by the improved sensitivity and speed in the qSTAR method, improved fluorescence signal, tighter replicates and increased speed.

During the initiation phase, the reaction is run at an elevated temperature, 62° C. This elevated temperature selectively inhibits the nicking enzyme without permanently damaging it functionally (as shown in conjunction with amplification and FIG. 9B, described elsewhere). During this initial phase, the polymerase is relatively favoured, allowing for rapid and specific extension, since the reaction temperature is relatively close to the optimum temperature of the polymerase.

After the initiation phase of the reaction the temperature is reduced to a temperature which is closer to the optimum temperature for the nicking enzyme, resulting in increased efficiency and allowing for increased generation of template. Since the desired template pathway has been favoured over errant pathways, specificity and sensitivity is greatly increased, which is further facilitated by qSTAR's temperature shuttling and selective activity regulation of the enzymes.

The reaction mixture is continuously shuttled between 62 and 57° C., to give a controlled, rapid amplification technology that can be utilized for accurate quantitation.

The novel non-isothermal amplification method of the invention provides a substantial improvement over many types of existing amplification reactions, including isothermal reactions and those that rely on high temperatures for duplex dissociation. By controlling enzyme activity by "temperature gating" and optimizing reaction kinetics, the method of the invention has improved consistency and control of amplification, whilst increasing the sensitivity of detection, to allow for reliable and accurate quantitation.

Example 3: Results Using 2'-O-Methyl Modified Primers

Figure 3:
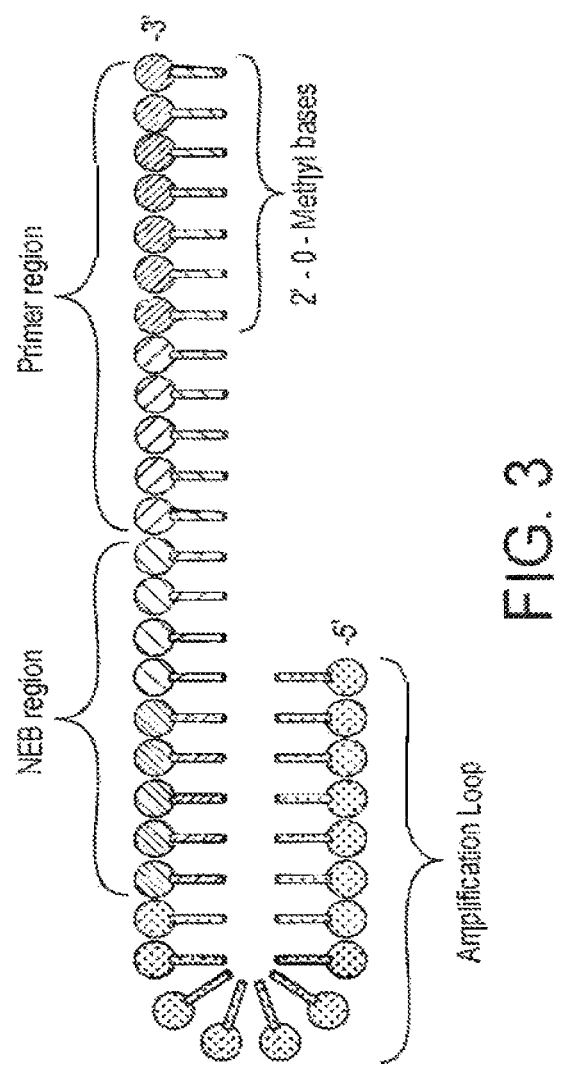
FIG. 3 is a schematic representation of a typical embodiment of a primer oligonucleotide molecule useful in performing the method of the invention.

As described in U.S. Pat. Nos. 6,794,142 and 6,130,038, the use of 2'-O-methyl modified primers is known to reduce primer dimer formation during amplification. US 2005-0059003 describes the use of 2'-O-methyl modifications located at the 3' end of SDA primers, suggesting that Bst DNA Polymerase I and derivatives can efficiently utilize 2'-modified ribonucleotides as primers for DNA synthesis. Target specific primer regions comprising one or more 2' modified nucleotides (e.g., 2'-O-methyl, 2'-methoxyethoxy, 2'-fluoro, 2'-allyl, 2'-O-[2(methylamino)-2-oxoethyl], 2'-hydroxyl (RNA), 4'-thio, 4'-CH3-O-2'-bridge, 4'-(CH3) 3-O-2'-bridge, 2'-LN A, and 2'-O—(N-methylcarbamate, 2'-Suc-OH)) should improve amplification reactions. The reactions were carried out using the enzyme-selective temperature shuttling (62-57° C.) as described in the preceding example along with a single 2'-O-methylated base or a string of 2'-O-methylated bases located toward the 3' of primers (illustrated schematically in FIG. 3).

Figure 5A:
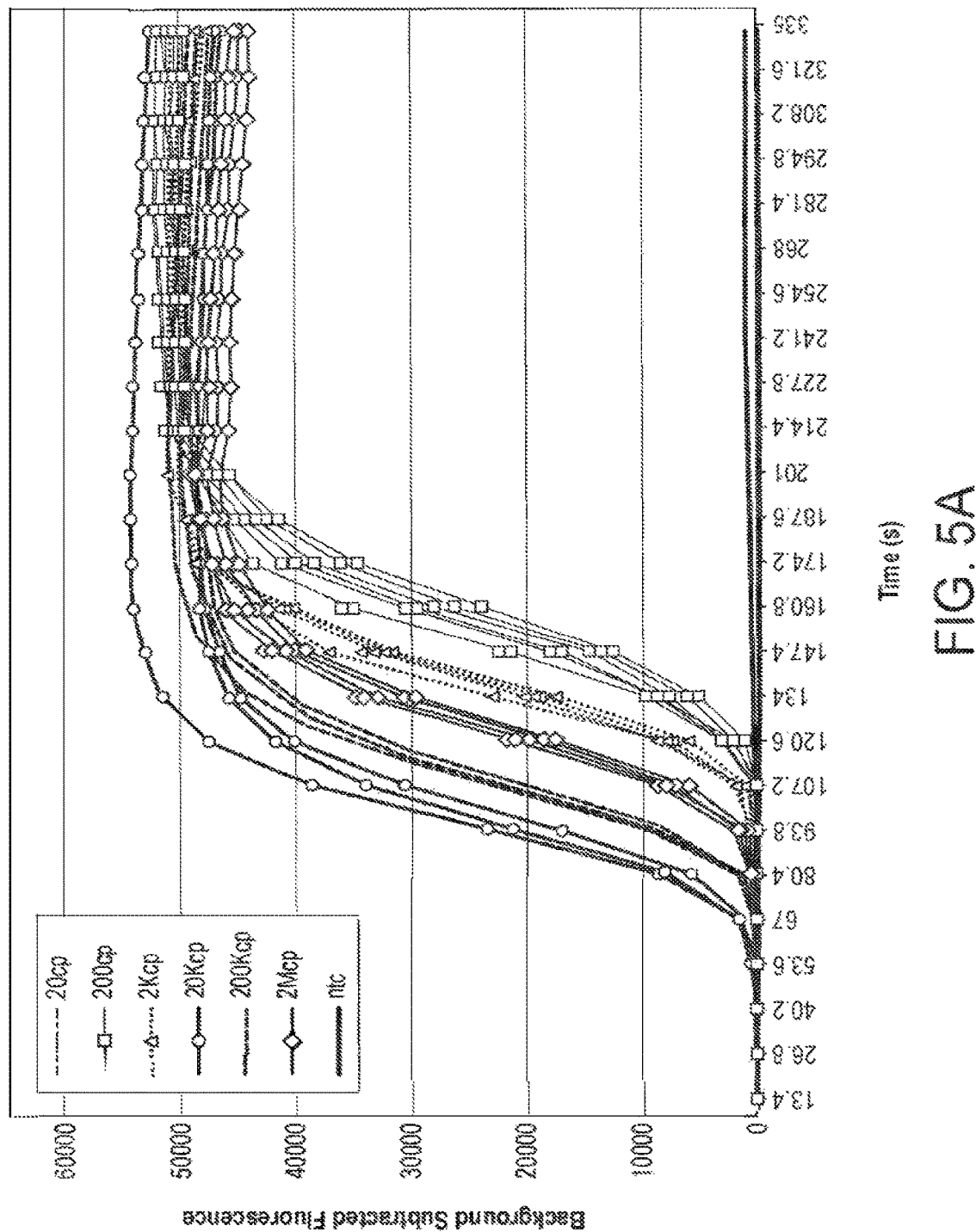
Figure 5B:
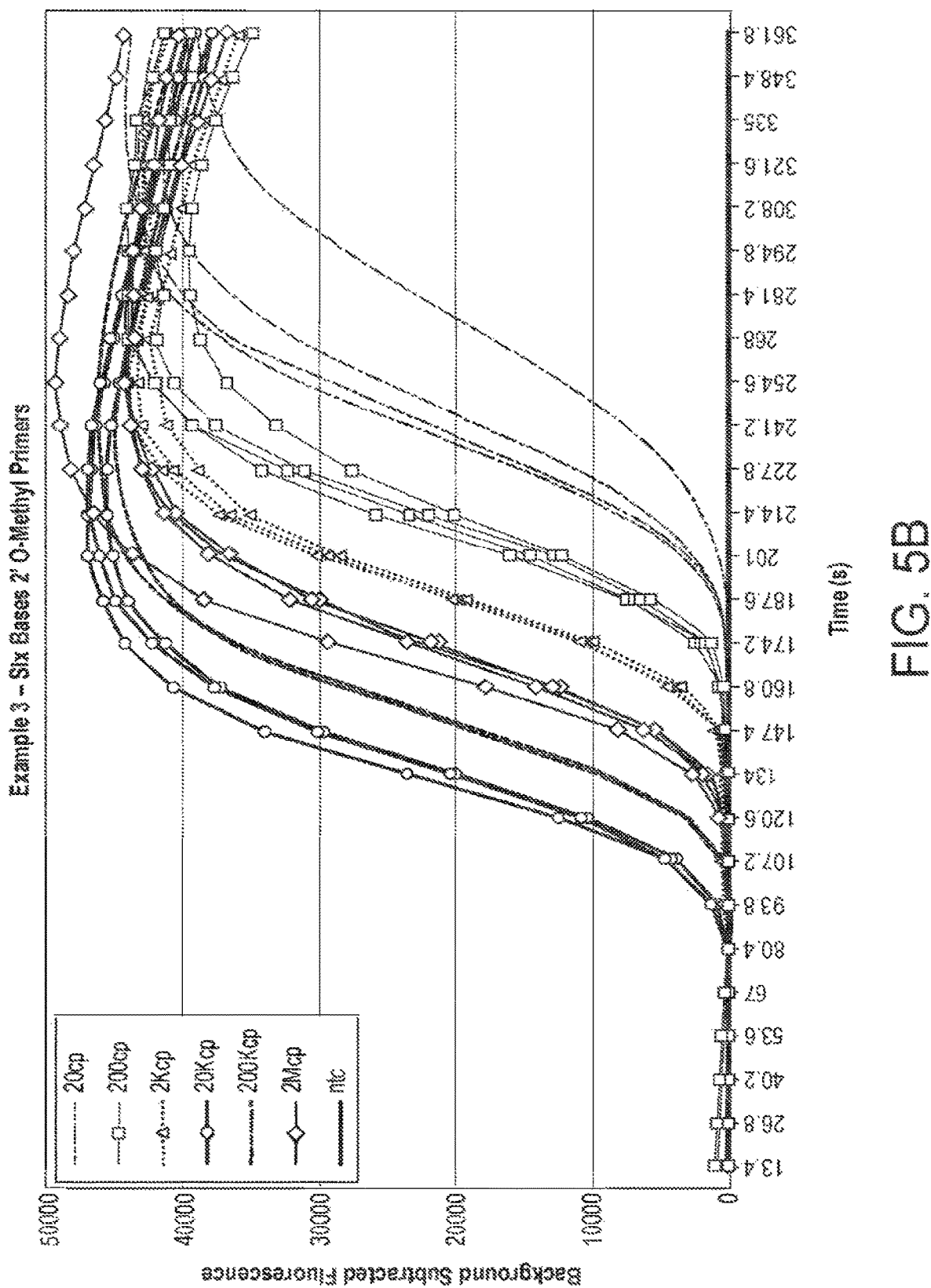

The results of amplification using primers comprising one or more 2' modified nucleotides at the 3' end are shown in FIGS. 5A-5C. Reactions were carried out with a minimum of four replicates across all five log input gDNA concentrations, along with no target control reactions. As demonstrated, the reactions are quantitative across a five-log range with a coefficient of determination greater than 0.99 (data omitted for brevity). The coefficient of determination was calculated by using a similar method as described by Pfaffl in "A new mathematical model for relative quantification in real-time RT-PCR", (2001, Nucl. Acids Res. 29 (9) e45). The starting point of the exponential phase, EP, of amplification was determined by identifying where EP began above background fluorescence. Background fluorescence was calculated by averaging the first three reads of each reaction. The EP was then determined based on when the relative florescence for each reaction reached 2,000. Using the known input for each reaction the EP was evaluated using a linear regression algorithm to determine the coefficient of determination across log values. This standard curve was generated and calculated for linearity, typically with qSTAR reactions generating a R squared valued 0.99 or greater.

The data demonstrate (FIG. 5A) that the use of a primer incorporating a single 2'-O-methylated nucleotide stalls amplification reactions, slowing the speed of the reactions for better resolution across all concentrations of input. Further, the use of the qSTAR method not only improved the use of 2'-O-methyl amplification, it illustrates the functionality of the method with known amplification modifications. As shown in FIGS. 5B and 5C, incorporation of additional 2'-O-methylated bases along the primer improves the separation of the amplification, or rise from baseline allowing for greater resolution, improving the quantitative ability of the technology. In essence, separation between each concentration is improved by the slowing of the reactions caused by use of 2'-O-methylated bases: for example, a reaction with a one cycle separation in rise from baseline, when using unmodified primers, shows a separation of 2 cycles when using primers incorporating the 2'-O-methylated bases. This suggests that although 2'-O-methyl modifications do reduce the production of non-specific, errant, amplification in the exemplified method of the invention, the greater benefit of these modifications is to control the rate of reactions so as to permit greater resolution and more quantitative amplification.

Without limiting the applicants to any particular theory, the potential improvements obtained by using one or more 2' modified nucleotides in the primer region are hypothesized to be largely due to enhancements in the initiation phase of amplification. During the initial extension phase, two events help to explain the activity of 2' modified nucleotides in the amplification reaction of the invention. First, 2'-O-methylated bases are known to lower the melting temperature of DNA/DNA duplexes resulting in more controlled initiation by tending to inhibit template::template interactions thereby reducing the opportunity for polymerase extension of nonspecific complexes formed by interactions between primers. Secondly, it is possible that the polymerase stalls as the nucleotide enters the binding pocket. In non-productive reactions (i.e., off-target or primer dimer formation), the stalling effect is sufficient in minimizing aberrant extension because template binding is near its melting temperature. Consequently, 2' modifications are able to restrict undesirable amplification pathways because the reaction has mired. qSTAR is able to leverage 2' modifications and better regulate target amplification for tuning reactions for improved quantitative ability. This polymerase stalling further explains why qSTAR in conjunction with 2'-O-methyl modifications improve each other. The initial polymerase temperature region found in the exemplified method of the invention, besides decreasing primer dimer formation, slows initiation in a controlled and reliable manner. Furthermore, since qSTAR repeatedly shuttles to a lower temperature, the reduction in melting temperature caused by 2' modifications can be curtailed as the reaction proceeds.

Example 4: Reproducibility

Figure 6:
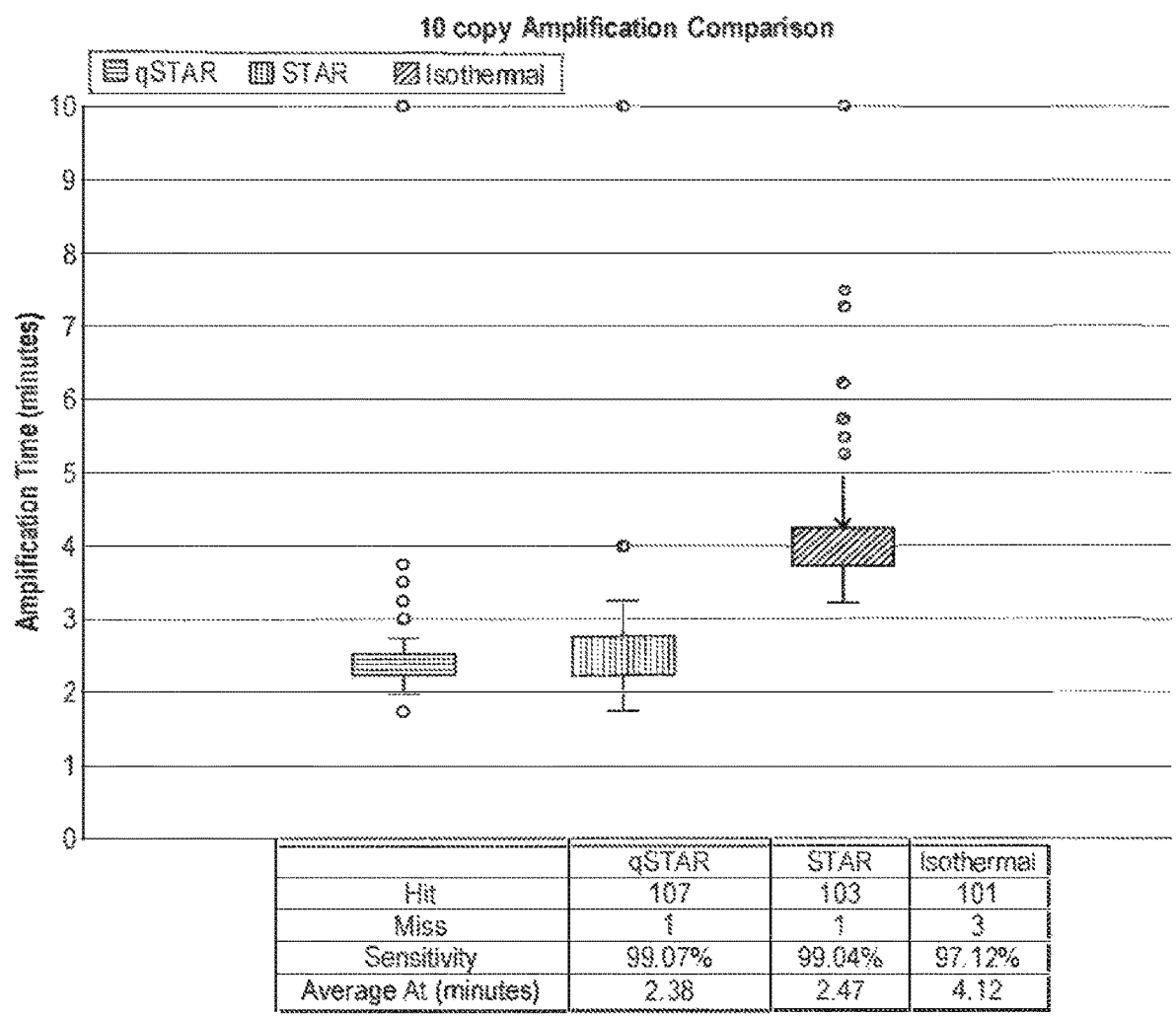
FIG. 6 is a scatter plot showing the average time to achieve amplification ($A_T$, in minutes), as judged by generation of a fluorescence signal above a background threshold, for a method in accordance with the invention (left hand plot), and a method performed in accordance with the STAR protocol disclosed in WO2018/002649 (middle plot), or an isothermal reaction protocol (right hand plot)

For validation of the qSTAR technology, a large replicate study was carried out comparing qSTAR performance, against the performance of STAR and other published isothermal conditions as described in U.S. Pat. No. 9,562,263. Amplifications, (qSTAR vs. STAR vs. Isothermal), were carried out using 100 plus replicates for reactions containing target and 16 replicates for control reaction mixtures without target. All conditions used the same buffers, polymerase, nicking enzyme and target. As shown in the scatter plot in FIG. 6, qSTAR and STAR amplification shows a clear improvement in average time ($A_T$) to achieve amplification to threshold level of fluorescence (TL), improved sensitivity, and a reduced standard deviation between replicates, compared to the isothermal amplification reaction. The $A_T$ time for reactions performed according to the invention was 2.38 minutes, whilst the $A_T$ value for reactions performed according to conventional isothermal protocols was 4.12 minutes, a difference which is statistically significant (two-tailed test). (Note—failed reactions are shown as having an amplification time of 10 minutes—the maximum time for which reactions were run). Furthermore, the qSTAR method is an improvement over the STAR method with regards to speed. The qSTAR technology demonstrated the tightest replicates, highest sensitivity, fastest amplification with the least number of outliers. Not to limit the applicant to any particular theory, the significant reduction in amplification time is thought to be due to the improved initiation of the reaction, allowing for more efficient low copy amplification, minimized primer-dimer events, and increased specific product extension which allows for faster product generation than previously disclosed methods. Tighter replicates are achieved by leveraging the activity of the nicking enzyme and polymerase generating multiple chances for specific, rapid, and controlled amplification of desired templates.

Example 5: qSTAR Functionality

A characteristic feature of the method of the present invention comprises the modulation of enzymatic activity by using small temperature changes during the amplification process, which temperature changes are far smaller than, say, the changes undergone during performance of qPCR. To verify that the nicking enzyme has reduced activity during the initiation phase, yet that it is highly active during the exponential phase, the inventors have developed two unique protein activity assays: a polymerase activity assay ("PAA"), and a nicking activity assay ("NAA").

Figure 7:
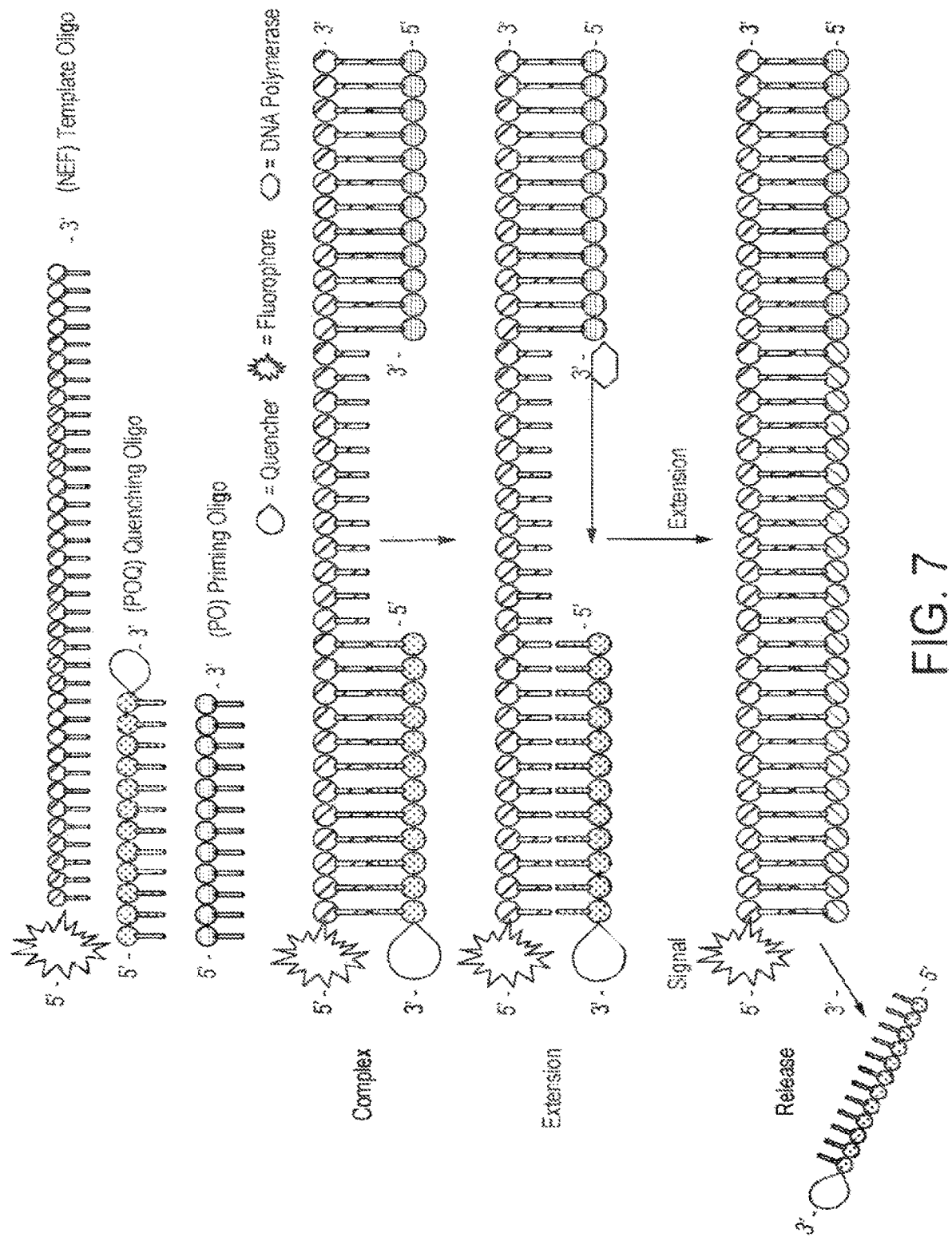
FIGS. 7 and 8 are schematic representations of, respectively, a polymerase activity assay and a nicking activity assay, of use in characterising the method of the invention.

Polymerase Activity Assay Design, Enzymes, and Oligonucleotides: Synthetic oligonucleotides for the PAA were synthesized by Integrated DNA Technologies (Coralville, Iowa). The design consists of three oligonucleotides; the template oligo (NEF), (SEQ ID NO: 4 5'-/56 FAM/ ACCGCGCGCACCGAGTCTGTCGGCAGCACCGCT-3'), priming oligo (PO), (SEQ ID NO: 5 5'-AGCGGTGCTGCCGACA-3'), and quenching oligo (POQ), (SEQ ID NO: 6 5'-GGTGCGCGCGGT/3BHQ_1/-3'). Together these three oligonucleotides form a complex in solution each with unique functions, as shown in FIG. 7. The NEF has a 5' fluorophore, POQ has a 3' quenching moiety that absorbs the photons released by the 5' template oligo fluorophore. The PO serves as the initiation site for a strand displacement polymerase to extend and displace the quenching oligo allowing for fluorescence to be generated due to the quenching oligo no longer being in proximity to the template oligo. Highly active strand displacing polymerases generate a fluorescent signal at an increased rate compared to less active polymerases or those that lack stand displacing activity.

Polymerase Activity Assay Conditions

The basic Polymerase Activity Assay (PAA) mixture contains a template oligo (NEF) with a 5'-FAM modification, a priming oligo (PO) which anneals to the template's 3'-end, a quenching oligo (POQ) with a 3'-BHQ1 modification which anneals to the template's 5'-end, and a polymerase under test (referenced above). The reactions were performed in a final volume of 25 µl, including 0.2 µM NEF, 0.3 µM PO, 0.7 µM POQ, and 1×PAA Master Mix. At a 1× concentration, the PAA master mix contains the following reagents; 12.5 mM MgSO4, 90 mM Tris-HCl (pH 8.5), 300 µM each dNTPs, 15 mM $NH_4CH_3CO_2$, 15 mM $Na_2SO_4$, 5 mM DTT, 0.2 mg/ml BSA, 0.02% TRITON® X-100, 20 mM $Rb_2SO_4$, 10 mM L-Threonine, and 0.03 U/µl polymerase. The reactions are run isothermally to determine the activity of selected enzymes at specific temperatures. The PAA was performed with the Agilent Mx3005P qPCR apparatus (Agilent). Every reaction had a pre-reaction incubation to allow the reagents to come to temperature to test the effect of the selected temperature and prevent any variation as reactions heated up. Each reaction assessed amplification kinetics, enzyme performance, and signal fluorescence.

Figure 8:
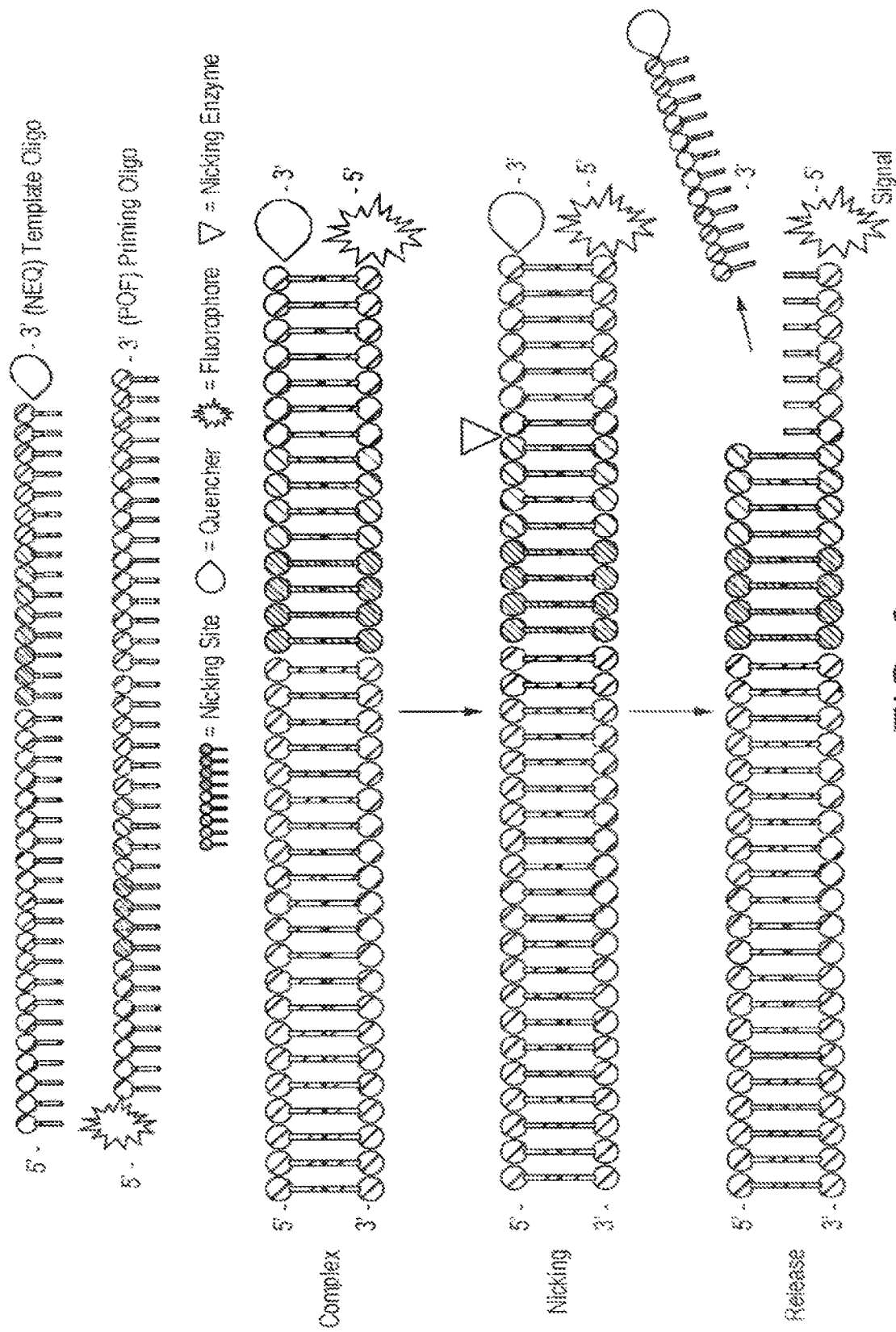

Nicking Activity Assay (NAA) Design, Enzymes, and Oligonucleotides:

Synthetic oligonucleotides for the NAA were synthesized by Integrated DNA Technologies (Coralville, Iowa). The assay involves two oligonucleotides; the template oligo (NEQ), (SEQ ID NO: 7 5'-ACCGCGCGCA CCGAGTCTGTCGGCA/3BHQ_1/-3') and priming oligo (POF, SEQ ID NO: 8 5'-/56-FAM/CTGCCGACA-GACTCGGTGCGCGCGGT-3'). Together these oligonucleotides form a complex in solution each with unique functions, as shown in FIG. 8. The template oligo has a nicking site for nicking endonuclease activity and downstream a 3' quencher. The priming oligo has the complementary nicking site sequence and a 5' fluorophore. When in solution the two form a complex that completes a nicking binding site allowing for the nicking endonuclease to cut. The oligonucleotide quencher 3' of the nick site, following a nick by a nicking endonuclease, now has a low melting temperature. Because the reaction is performed above this melting temperature, the shortened fragment containing the quencher is released from the complex, resulting in unquenched fluorescence. The more active the nicking enzyme the faster and greater the florescent signal is generated.

Nicking Activity Assay Conditions

The basic NAA mixture contains the template oligo (NEQ) with a 3'-BHQ1 modification, and the priming oligo (POF) with a 5'-FAM modification which anneals to the template, and a nicking endonuclease to be tested. The reactions were performed in a final volume of 25 µl, including 1.3 µM NEQ, 1.6 µM POF, and 1×NAA Master Mix. At a 1× concentration, the NAA master mix contains the following reagents; 12.5 mM $MgSO_4$, 90 mM Tris-HCl (pH 8.5), 15 mM $NH_4CH_3CO_2$, 15 mM $Na_2SO_4$, 5 mM DTT, 0.2 mg/ml BSA, 0.02% TRITON® X-100, 20 mM $Rb_2SO_4$, 10 mM L-threonine, and 0.008 U/µl nicking endonuclease. The reactions are run isothermally to determine the activity of selected enzymes at specific temperatures. The NAA was performed with the Agilent Mx3005P qPCR apparatus (Agilent). Every reaction had a pre-reaction incubation to allow the reagents to come to temperature to test the effect of the selected temperature and prevent any variation as reactions heated up. Each reaction assessed amplification kinetics, enzyme performance, and signal fluorescence.

Temperature Profile of Enzymes

Figure 9A:
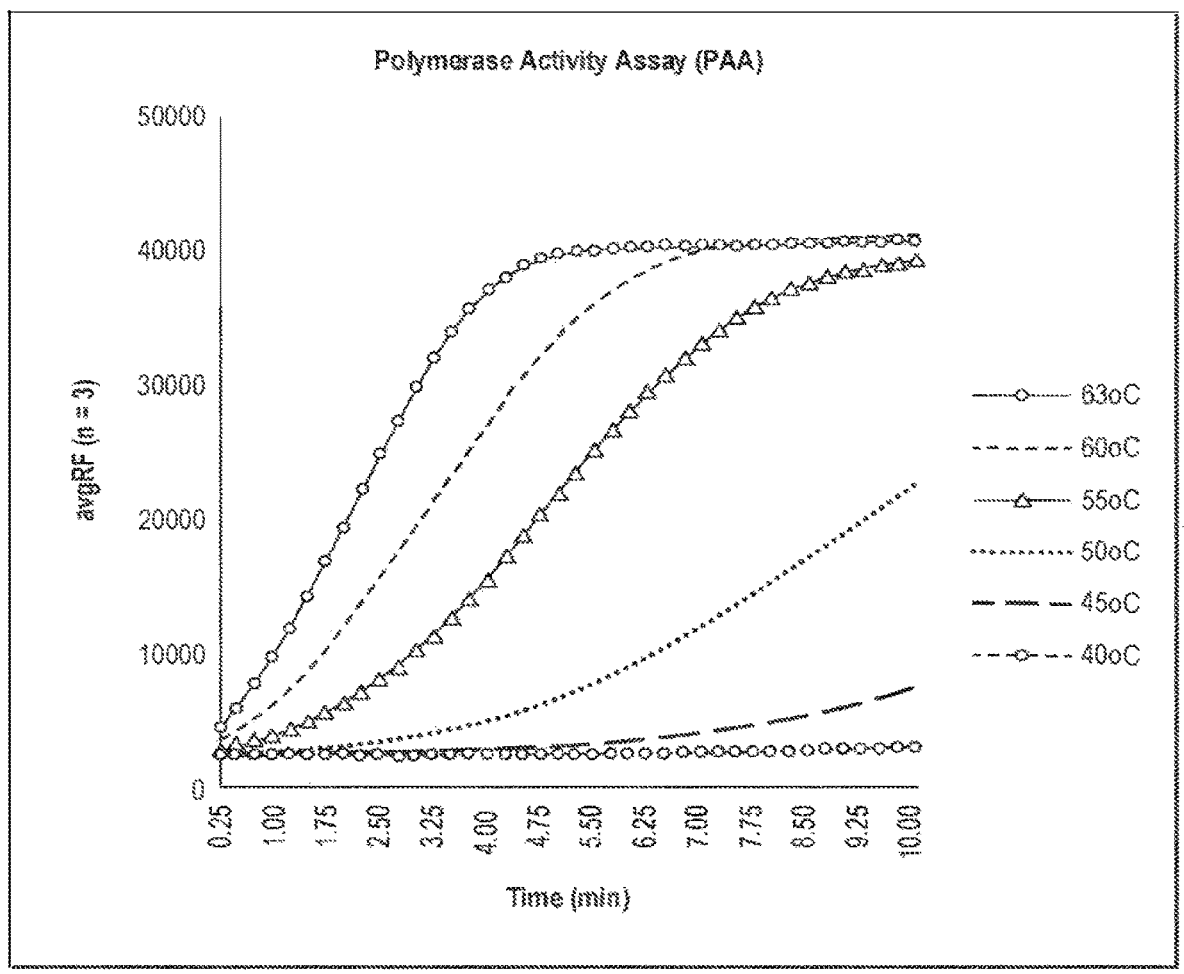
FIGS. 9A and 9B are graphs of average (of three replicates) of relative fluorescence (in arbitrary units) against time (in minutes) of a polymerase activity assay (FIG. 9A) or a nicking activity assay (FIG. 9B), conducted at a variety of temperatures.

FIG. 9A shows the polymerase activity assay for six isothermal conditions. At 63° C. the polymerase has the strongest activity and kinetics, as determined by the slope of the fluorescent curve and total fluorescence. Each subsequent drop in temperature, 60° C., 55° C., 50° C., and 45° C. shows a decrease in activity until arriving at 40° C. At this low temperature, the activity of the polymerase appears to be substantially non-existent.

Figure 9B:
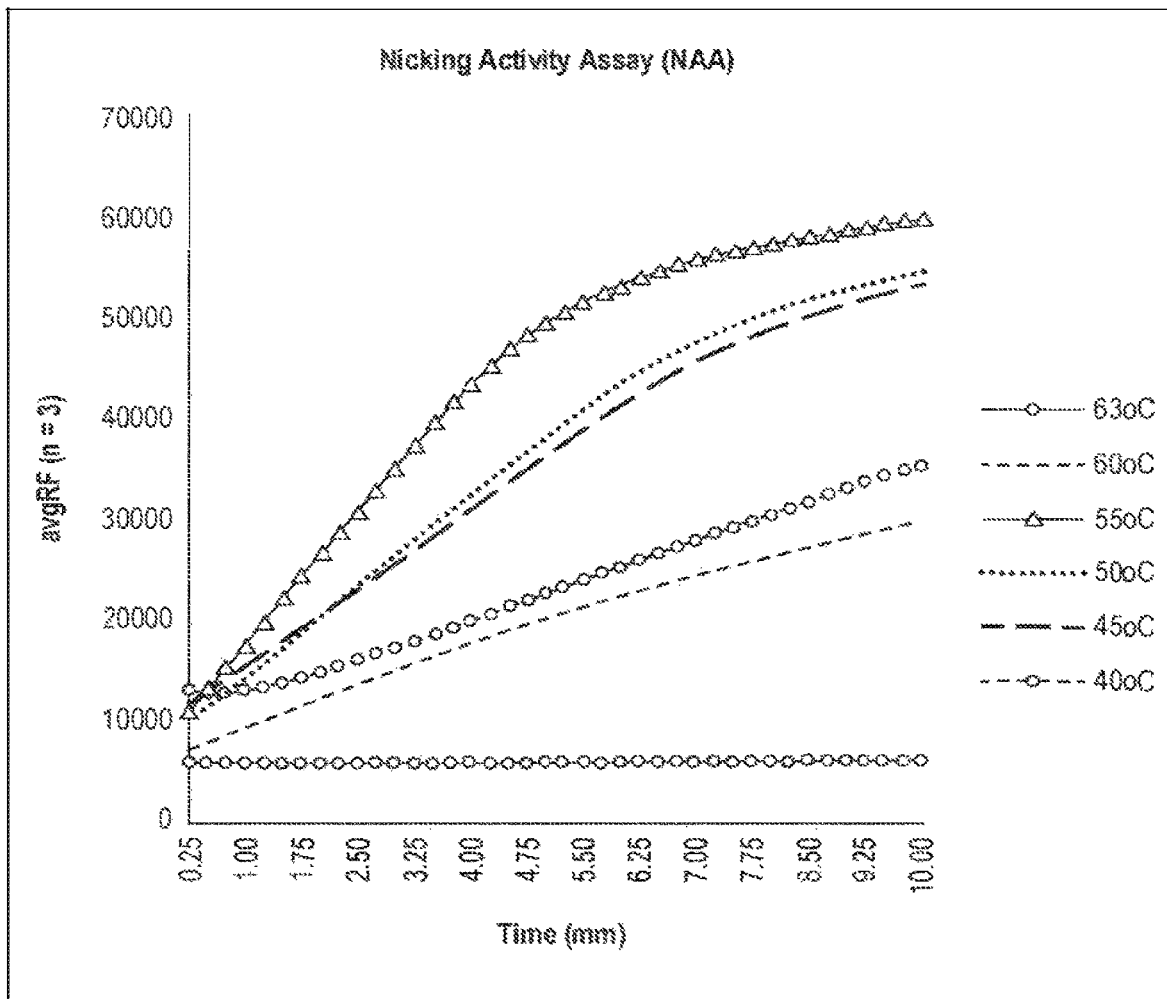

FIG. 9B shows the nicking activity assay for six isothermal conditions. Unlike the polymerase assay, which shows a clear optimal temperature towards the top end of the preferred range of temperatures for the qSTAR method, the nicking activity assay shows an optimum (about 55° C.) towards the lower end of the preferred range of temperatures for the qSTAR method, while demonstrating little to no activity at 63° C. All other temperatures show some level of activity for the nicking enzyme.

The data from these assays demonstrate the distinctive nature of the qSTAR technology. Unlike other amplification methods that rely on strand displacement and/or temperature separation, qSTAR uniquely uses "temperature gating" to modulate enzyme activity and control rapid amplification. Recognizing the unique features of these enzymes and temperature dependence upon activity, the inventors have developed a new rapid, specific, controlled amplification technology that can quantitate unknown sample inputs in under six minutes.

Without being bound by any particular theory, it is believed that in this example qSTAR involves activity modulation of the nicking enzyme as it amplifies between two temperatures. 63° C. and 57° C. are the preferred temperature choice in the exemplified system described above (based upon current protein activity profiles) because they allow for controlled amplification, a requirement for any quantitative technology. It is further believed that controlling the activity of either enzyme is desirable to manage a known efficient amplification event for quantitation of unknown nucleic acid material.

Example 6: qSTAR Amplification Results Using qPCR Polymerases

To demonstrate the unexpected properties of qSTAR versus other amplification technologies, such as PCR, a comparison of common PCR polymerases was performed, showing that common PCR polymerases and methods are inactive in the qSTAR method. Four PCR polymerases; VENT™, DEEP VENT™, Taq, and PHUSION were used for amplification in a qPCR method, as described below, and compared with the qSTAR method. Because molecular beacons only measure an increase in the total amount of specific single-stranded DNA product, non-specific amplification product is not measured independently of the intended amplification product. To measure the production of all amplification products (e.g. including those arising from primer dimer formation), reactions were carried out in the presence of SYBR® Green I. SYBR® Green I is one of the most sensitive dyes known for detecting single-stranded DNA, RNA, and double-stranded DNA. Because SYBR® Green I has a low intrinsic fluorescence, it is a good choice for detection of total amplification in a reaction, both specific and non-specific, to demonstrate that common PCR polymerases are inactive in the qSTAR method.

qPCR/qSTAR Assay Design, Master Mix, and Oligonucleotides:

Synthetic oligonucleotides for the in-house qPCR assay (Ctx) were synthesized by Integrated DNA Technologies (Coralville, Iowa) and designed for the amplification of Chlamydia Trachomatis genomic DNA. The design consists of two oligonucleotides; the forward priming oligo (Ctx_L.F1, SEQ ID NO: 9 AAAAAGAT-TTCCCCGAATTAG), and a reverse priming oligo (Ctx_L.R1_3'(-2), SEQ ID NO: 10 AGT-TACTTTTTCCTTGTTT). Oligonucleotides were synthesized by Integrated DNA Technologies (Coralville, Iowa). SYBR® Green I Nucleic Acid Stain (Lonza Rockland, Inc. P/N 50513) was used as an intercalating dye for detection of double stranded DNA (dsDNA) products. PCR master mix and polymerases used were from New England Biolabs (Ipswich, Mass.); 10× THERMOPOL® Reaction Buffer, VENT™ (exo-) DNA Polymerase (P/N M0257S), DEEP VENT™ (exo-) (P/N M0257S), and Taq DNA Polymerase (P/N M0267S), 5× PHUSION HF Buffer, and PHUSION HF DNA Polymerase (P/N M0530S). Genomic DNA for Chlamydia Trachomatis (Strain: UW-36/Cx) (P/N VR-886D) was purchased through ATCC (Manassas, Va.).

qPCR/qSTAR Assay Conditions

The basic in-house qPCR assay (Ctx) mixture contained a forward primer oligo, a reverse primer oligo, a dsDNA intercalating dye, a known concentration of genomic DNA template, a 1× concentration of commercial PCR master mix, and its corresponding polymerase (mentioned above). The reactions were performed in a final volume of 25 µl, including 0.3 µM F1, 0.3 µM R1, 0.1×SYBR® Green I, 1× commercial PCR Master Mix, 0.03 U/µl polymerase, and 5,000 copies of genomic DNA template.

The in-house qPCR assay was run using 2 methods; a temperature profile replicating qSTAR technology or that of conventional qPCR. In the qSTAR method, the temperature of the reactions was controlled between two discreet temperatures to take advantage of enzyme activities. The initiation phase, substantially (polymerase only activity), was at the elevated temperature of 62° C. for two seconds. The exponential phase, (polymerase and nicking enzyme activity), was closer to the optimal temperature for the nicking enzyme's activity at 57° C. for five seconds. The total time for a complete shuttle was 15 seconds, which is more than double the dwell times at the maximum and minimum temperature due to the limits of the apparatus in changing temperature. The qPCR reactions were preformed using a 2-step program; 95° C. for fifteen seconds followed by 60° C. for sixty seconds, cycle 50× times. Amplification and qSTAR product detection were performed with the Agilent Mx3005P qPCR apparatus (Agilent).

Results

Figures 10A, 10B:
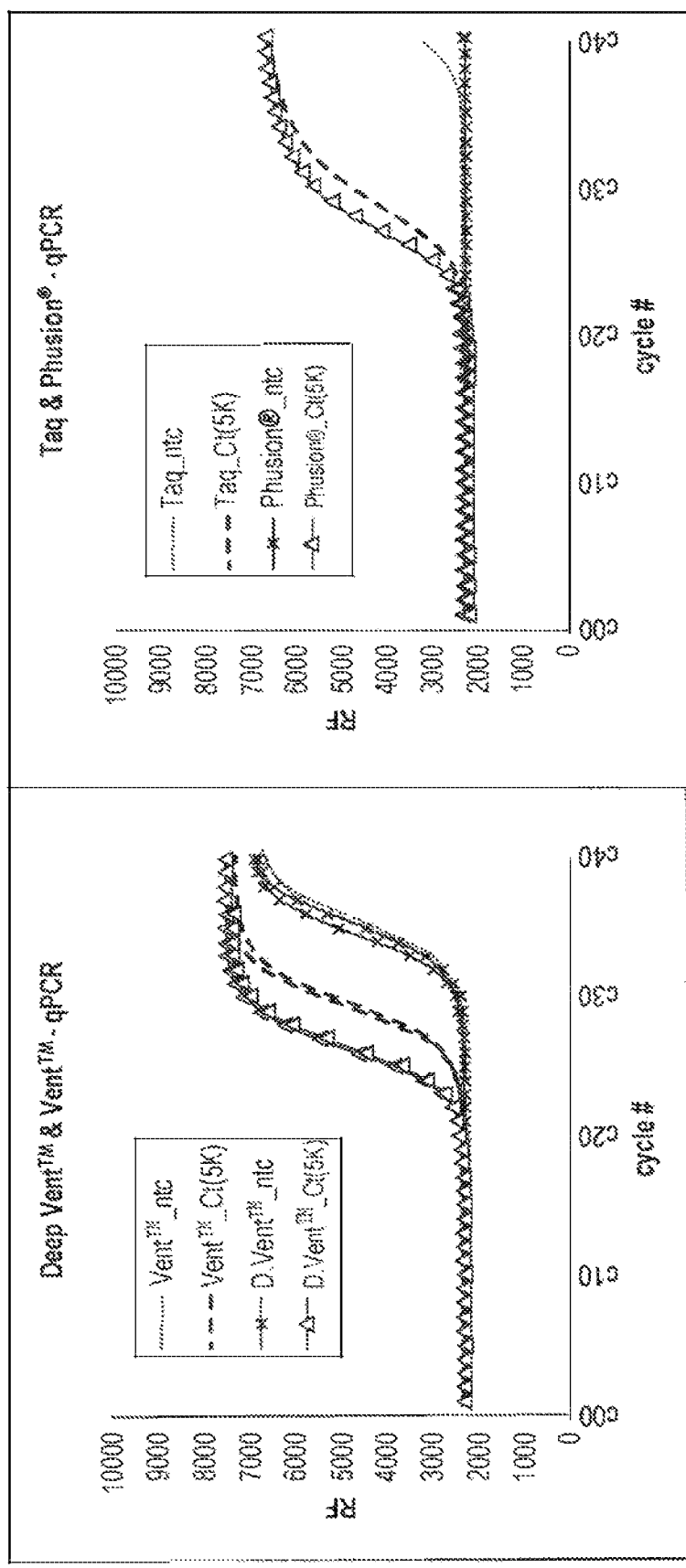
Figure 11A:
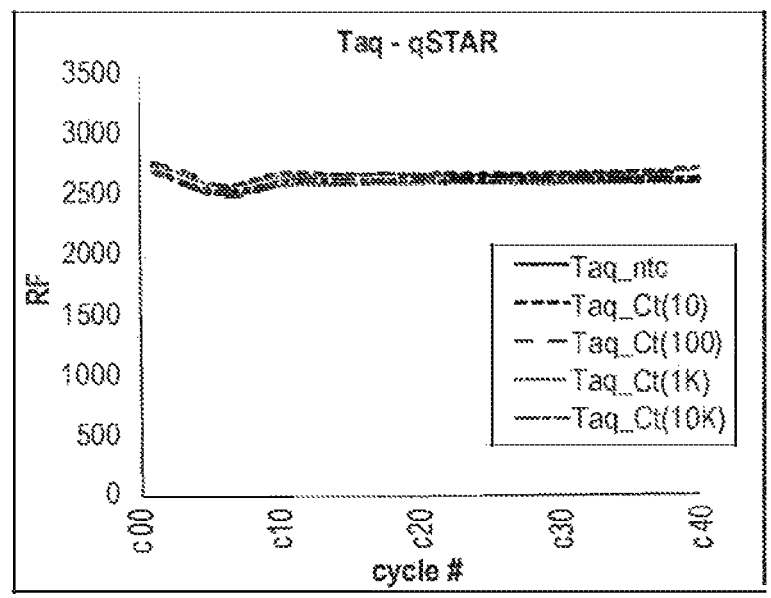
Figure 11B:
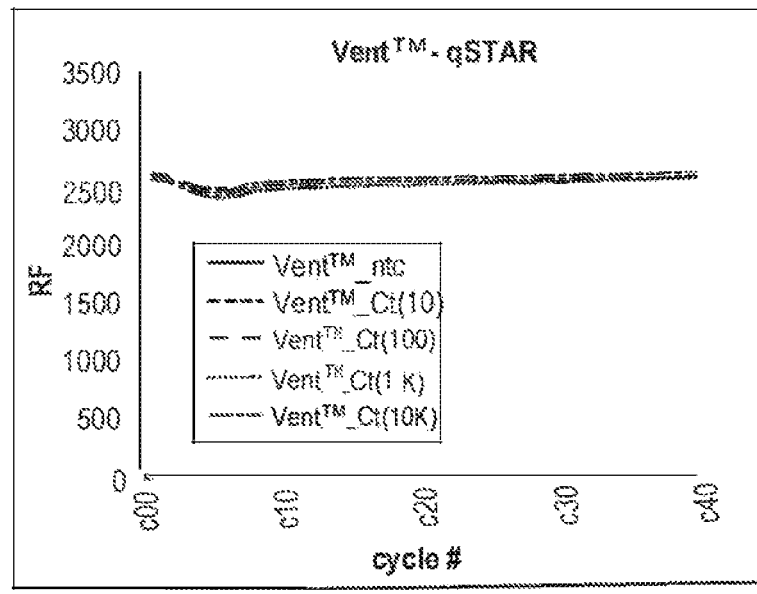
Figure 11C:
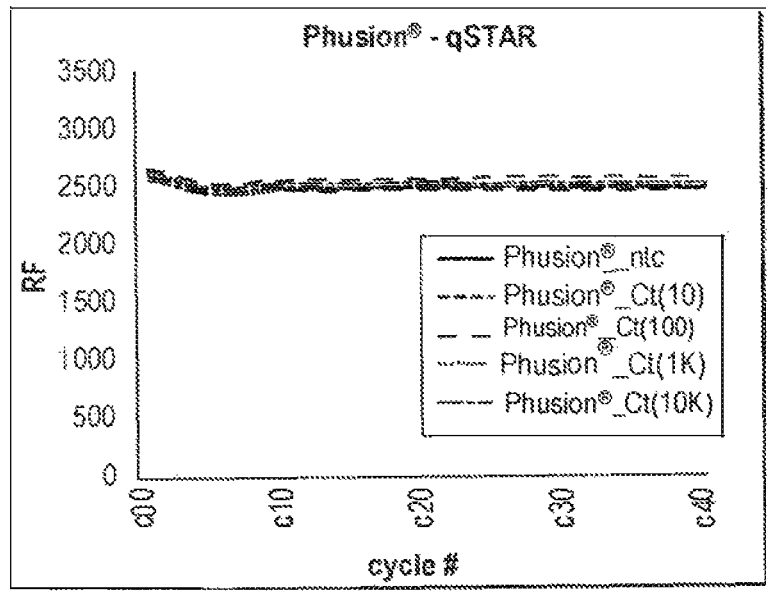
Figure 11D:
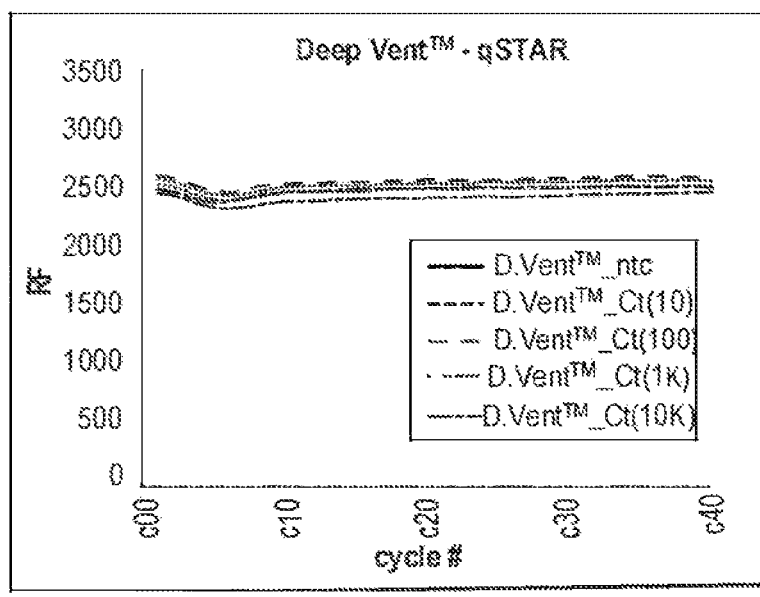

In FIGS. 10A-B show the real time data for qPCR amplification of five thousand copies of genomic Chlamydia trachomatis DNA compared to No Target control ("ntc"). Clearly seen is the amplification or activity of all polymerases using this qPCR method. It should also be noted that three out of the four polymerases show activity in the no target conditions, which is probably due to primer dimer formation. If the qSTAR method were similar to qPCR or previously reported thermal cycling amplification technologies, one would expect all or at a minimum one of these polymerases being active using the qSTAR method.

In FIGS. 11A-11D, the real time data demonstrate the inability of all four of the aforementioned polymerases to show any activity in reactions with no target or using 10, 100, 1K, 10K copies of genomic Chlamydia trachomatis DNA under the qSTAR temperature shuttling protocol. It is surprising that not one of these polymerases, all being used in their optimal temperature ranges, is able to show even a small amount of activity during the course of the incubation. Not to limit the inventors to any particular theory, this is believed to be due to following; (a) qSTAR conditions require strand displacement polymerases working in conjunction with nicking enzymes; without this combination of enzymes, amplification cannot proceed because product turnover is unable to progress; and (b) PCR and other cycling methods rely on elevated temperature (~95° C.) to strand-separate amplicons for amplification progression; since the qSTAR method does not use such an elevated temperature and instead uses more moderate temperature shuttling for controlling enzyme activity (rather than for strand separation), it could help explain the inability of any of these enzymes to show any activity in the qSTAR protocol conditions.

Example 7: qSTAR Versus qPCR Results

To demonstrate the quantitative nature of qSTAR, a comparison was performed versus qPCR. If qSTAR is quantitative one would expect the technology to have a high coefficient of determination, and be able to correctly predict the amount of genomic DNA in blinded samples as compared to qPCR.

C. trachomatis qPCR Assay Design, Master Mix, and Oligonucleotides:

Synthetic oligonucleotides (1) for the C. trachomatis qPCR assay (CtP) were designed for the amplification of Chlamydia Trachomatis genomic DNA. The assay involves the use of three oligonucleotides; a forward priming oligo, a reverse priming oligo, and a dual-labelled probe. Oligonucleotides were synthesized by Integrated DNA Technologies (Coralville, Iowa). The PCR master mix used, PRIME-TIME® Gene Expression Master Mix (P/N 1055770), was purchased from Integrated DNA Technologies (Coralville, Iowa). Genomic DNA for Chlamydia Trachomatis (Strain: UW-36/Cx) (P/N VR-886D) was purchased through ATCC (Manassas, Va.).

C. trachomatis qPCR Assay Conditions

The basic qPCR assay (CtP) mixture contained two primers, polymerase and genomic DNA. The reactions were performed in a final volume of 25 µl, including 0.3 µM forward primer, 0.3 µM reverse primer, 0.1 µM dual-labelled probe, 1× commercial PCR Master Mix, and various concentrations of genomic DNA template starting from 100,000 copies. Standard curves were generated using 10-fold dilutions of the genomic DNA. The qSTAR was performed as previously described along with the above standard curves.

The qPCR reactions were performed using a 2-step program; 95° C. for fifteen seconds followed by 60° C. for sixty seconds, cycle 50× times.

Results

Figure 12:
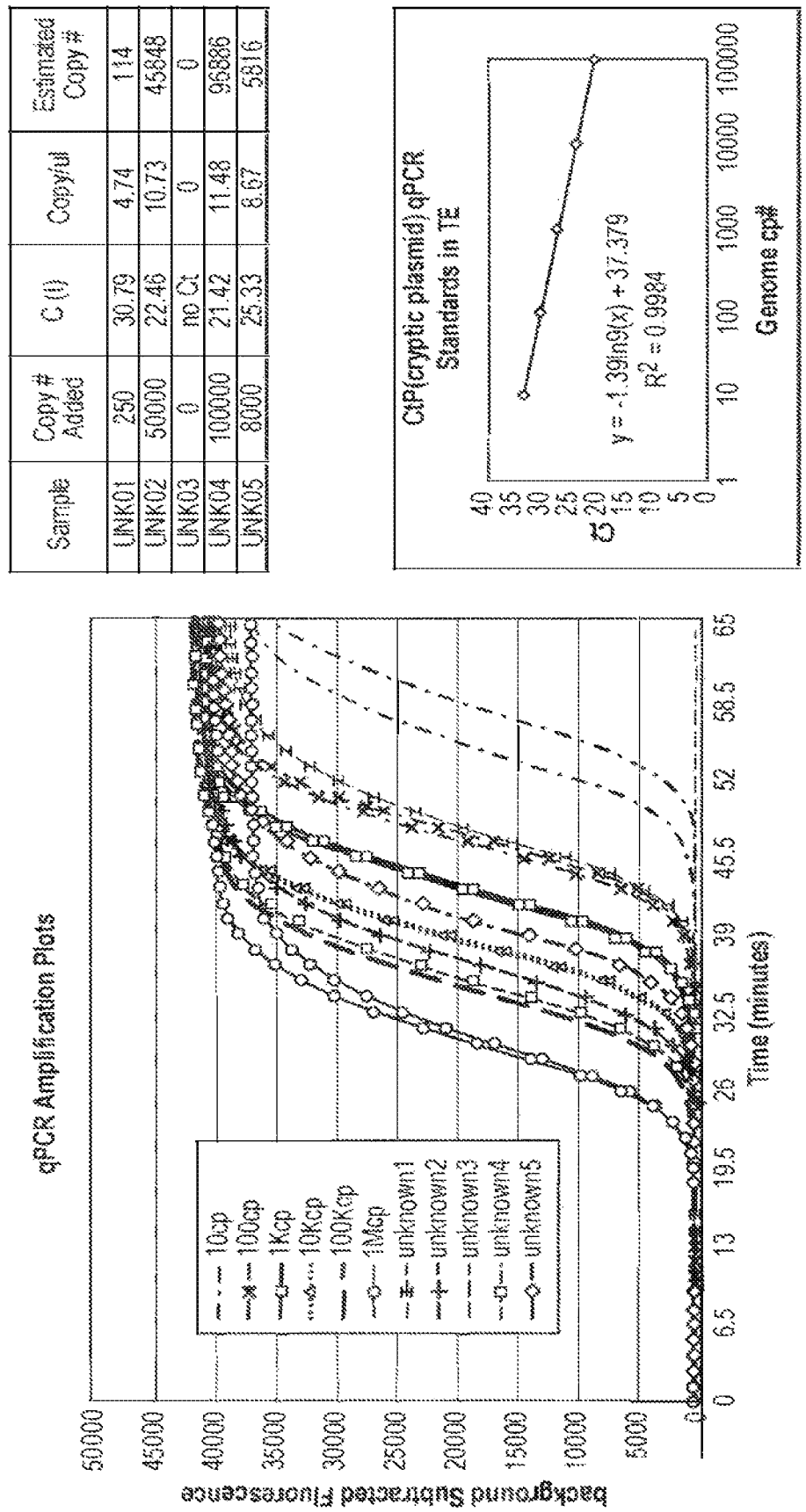
Figure 13A:
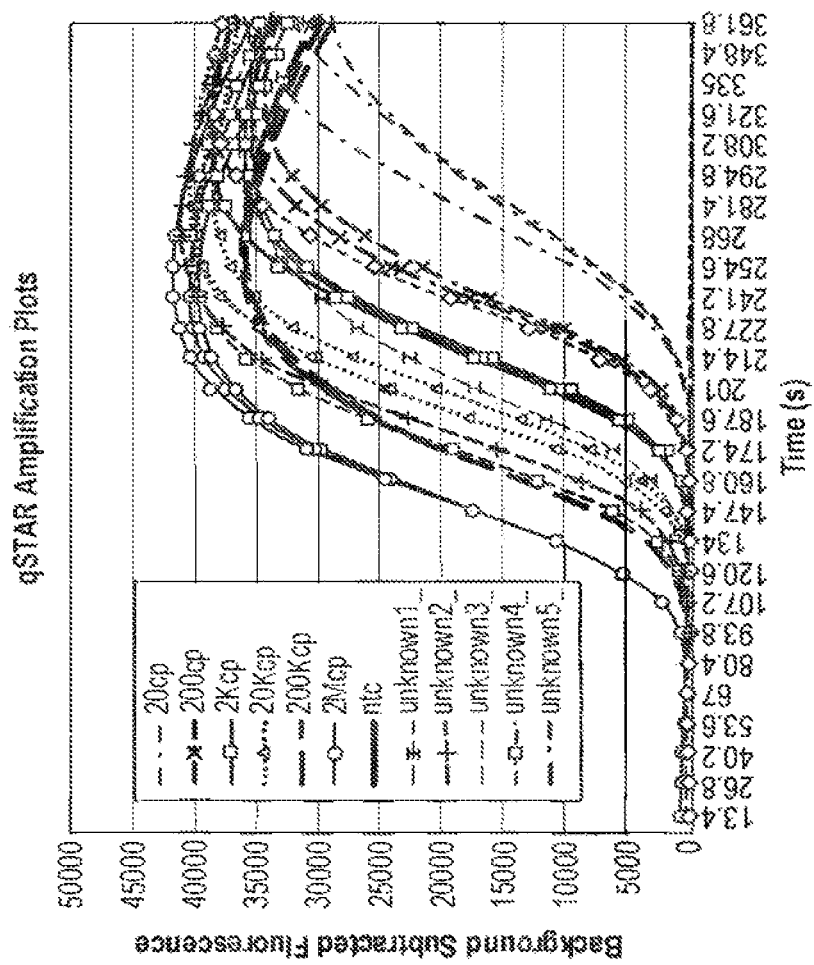
Figure 13A:
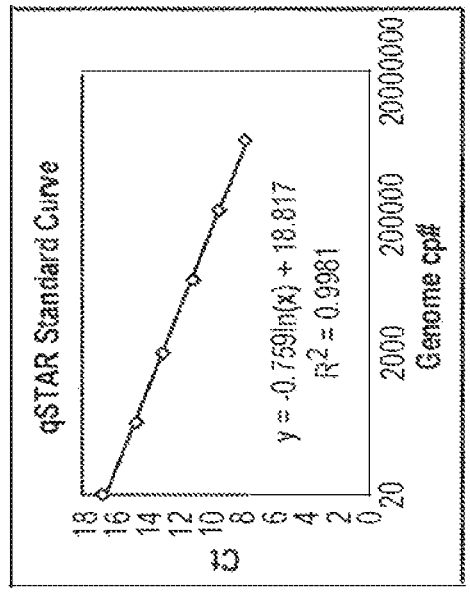

FIG. 12 shows the qPCR real time data for the standard curve and 5 unknown samples. The coefficient of determination for the standard curve was 0.9984, across a 5 log range. qPCR was able to correctly call all five unknown samples. FIG. 13 shows the qSTAR real time data for the standard curve and five unknown samples. The coefficient of determination for the standard curve was 0.9981, across a 6 log range. qSTAR was able to correctly call all five unknown samples. Table 2 shows a summary comparison of the two technologies, it is clear from the summary that qSTAR is comparable to qPCR when using the technology for quantitation.

TABLE 2

| Sample | Copy # Added | qPCR Estimated Copy # | qSTAR Estimated Copy # |
|---|---|---|---|
| UNK01 | 250 | 114 | 276 |
| UNK02 | 50000 | 45848 | 75699 |
| UNK03 | 0 | 0 | 0 |
| UNK04 | 100000 | 96886 | 140611 |
| UNK05 | 8000 | 5816 | 10630 |

Example 8: qSTAR Elevated Temperature Ranges

A further benefit of qSTAR technology is the ability to amplify across various temperature ranges. As described in U.S. Pat. Nos. 5,712,124, 9,562,263, 5,399,391, and 6,814,943, most technologies have a tight temperature range in which amplification can occur, and deviating from these ranges inhibits the reaction. To demonstrate the versatility of qSTAR, amplifications were carried out as described in Table 3 below.

TABLE 3

| qSTAR Conditions | | | |
|---|---|---|---|
| Initiation Phase | Time | Exponential Phase | Time |
| 63° C. | 1 second | 57° C. | 5 seconds |
| 64° C. | 1 second | 57° C. | 5 seconds |
| 65° C. | 1 second | 57° C. | 5 seconds |
| 66° C. | 1 second | 57° C. | 5 seconds |

Figure 14A:
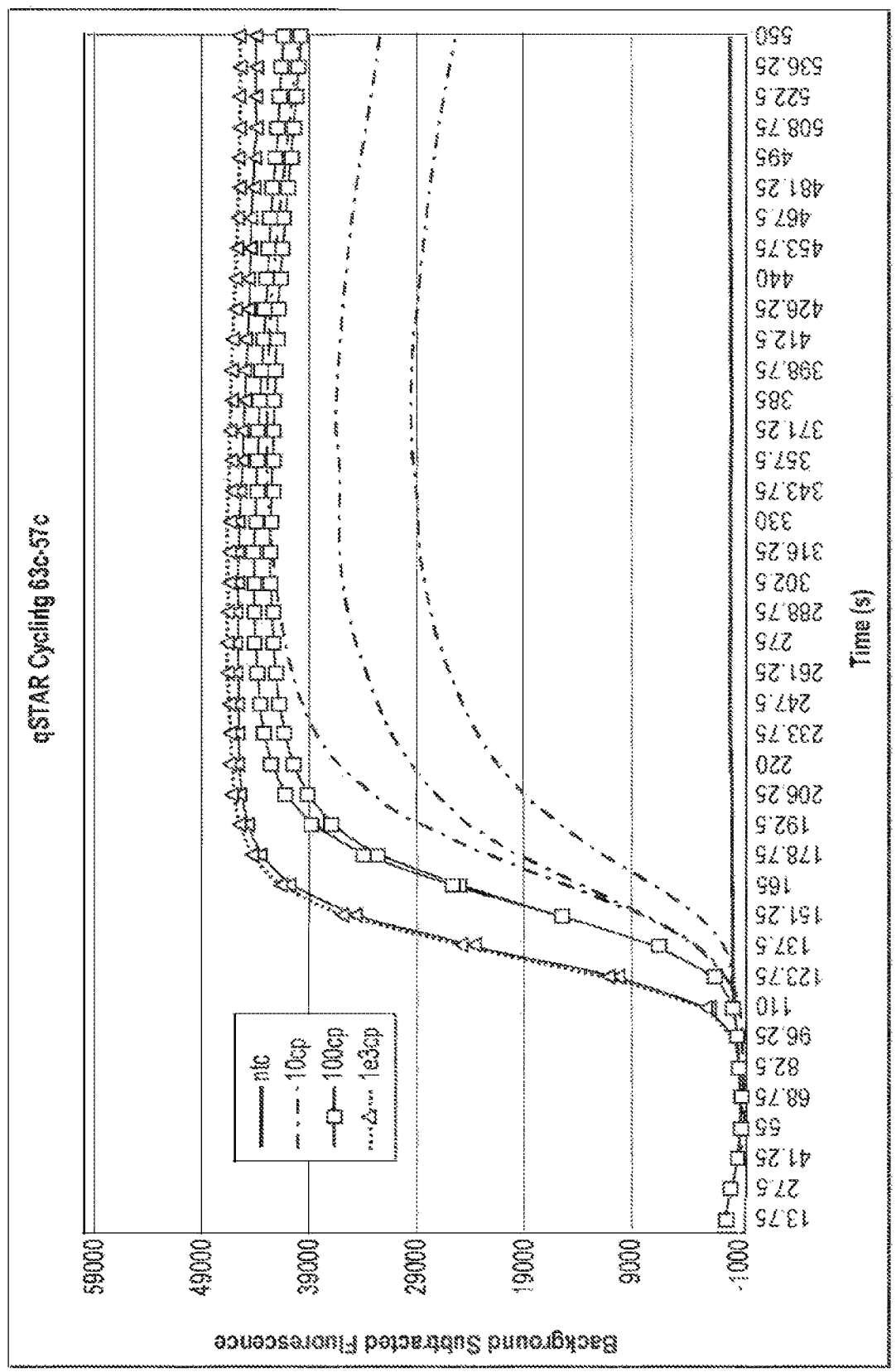
FIGS. 14A-14D are graphs of fluorescence (arbitrary units) against time (seconds), showing the results of amplification reactions performed according to the method of the invention over different temperature ranges.
Figure 14B:
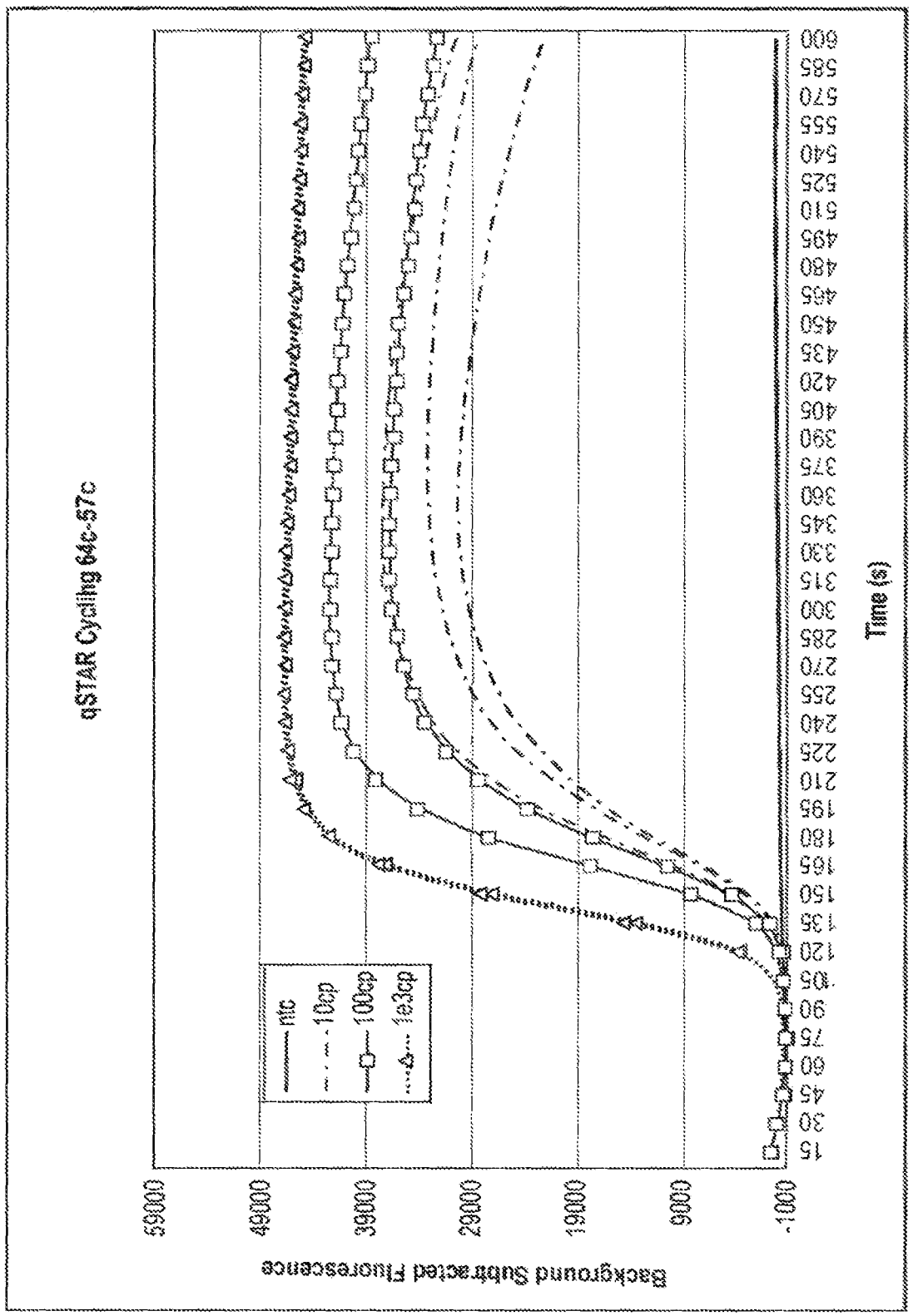
Figure 14C:
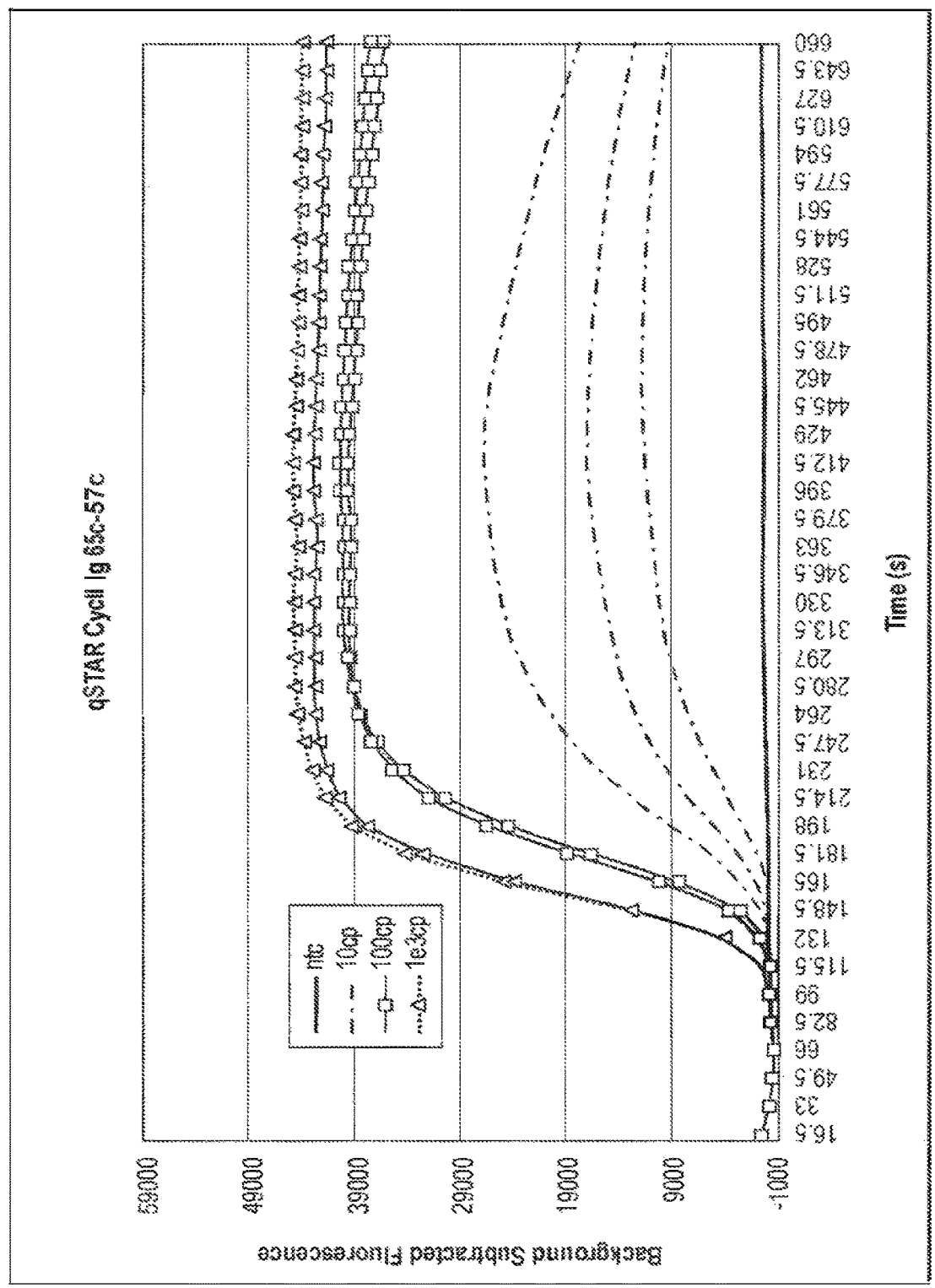
Figure 14D:
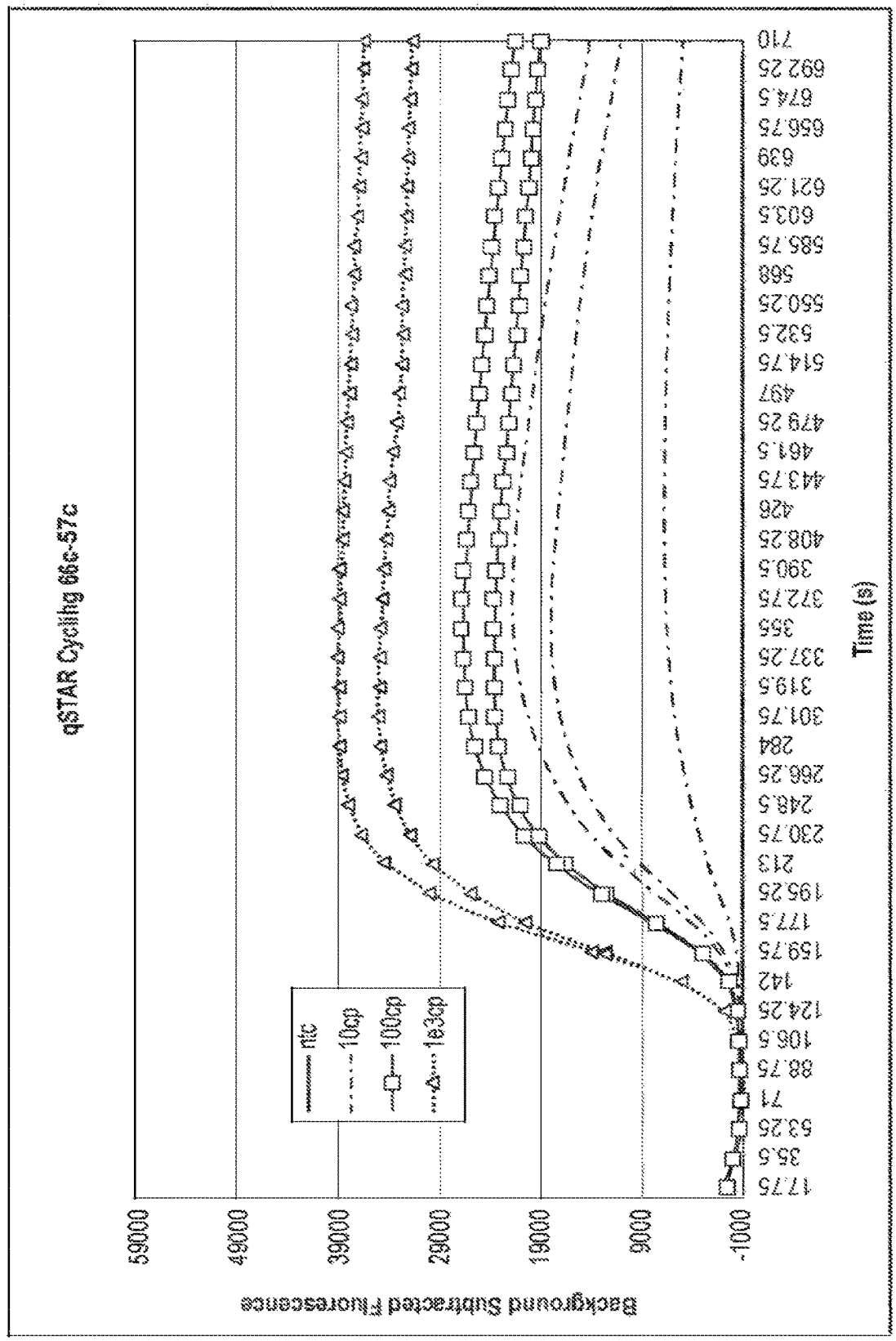

FIGS. 14A, 14B, 14C, and 14D are graphs of fluorescence (arbitrary units) against time (minutes). FIG. 14A shows the results for reactions starting at 63° C. FIG. 14B shows the results for reactions starting at 64° C. FIG. 14C shows the results for reactions starting at 65° C. and FIG. 14D shows the results for reactions starting at 66° C. In all cases, "no target" negative control reactions did not generate any fluorescence signal, whereas there was good amplification for 10, 100, and 1,000 copies. Although the fluorescence signal was slightly higher for the 63° C. reaction, all temperature conditions demonstrated strong amplification in less than 3 minutes. As long as enzyme modulation is achieved the qSTAR method can amplify well. It is believed that any temperature above 62° C. significantly reduces nicking enzyme activity (in respect of the exemplified nicking enzyme, Nt. Bst NBI).

Example 9: qSTAR Outside Known Temperature Ranges

Quantitative Polymerase Chain Reaction (qPCR) as described in U.S. Pat. No. 6,814,943 describes temperature ranges for thermal cycling. Typically for qPCR the following procedure is undertaken: denaturation around 95° C., annealing around 55° C., extension around 70° C. It would be surprising and unexpected if a technology could amplify in distinctly different temperature regions. Furthermore, individuals with knowledge in the art would not expect such a large temperature window for a technology to work in. WO 2011/030145A1 describes "wobbling" in which the assay temperature oscillates around a published isothermal temperature setpoint of no more than 15° C., but more preferably around 5° C. This temperature "oscillation" for some isothermal technologies has allowed for improved amplification kinetics. It would be surprising if qSTAR is able to work in dramatically different temperature ranges and still achieve amplification.

Amplification Conditions

The low temperature qSTAR mixture contained two primers (SEQ ID NO: 11 (5'-tGACTCCAcAcGGAGTCat-aaATCCTGCTGCmUA-3') and SEQ ID NO: 12 (5'-TGACTCCAcAcGGAGTCAGAACCAACAAGAAGA-3')), ISOPOL™ polymerase supplied by ArticZymes (Tromso, Norway), and nicking enzyme (referenced previously). The reactions were performed in a final volume of 25 µl, including 1.0 µM of the forward primer, 0.5 µM of the reverse primer, 0.25 µM molecular beacon (SEQ ID NO: 13 (5'-/56-FAM/tgaggTGCTGCTATGCCTCA/31ABkFQ/-3')), 10 µl qSTAR Master Mix and 5 µl DNA sample. qSTAR master mix contained the following reagents; 12.5 mM MgSO4, 90 mM Tris-HCl (pH 8.5), 300 µM each dNTPs, 20 mM NH4OAc, 30 mM NaOAc, 2 mM DTT, 0.02% TRITON® X-100, 12.5U nicking endonuclease, 75U polymerase. The temperature of the reactions was controlled between two discreet temperature phases to take advantage of inherent enzyme activities. The exponential phase, consisting primarily of polymerase and nicking activity, was at the elevated temperature of 45° C. for two seconds. The initiation phase, in which the polymerase is highly active and nicking enzyme has greatly reduced activity, was held at 38° C. for five seconds. The total time for a complete shuttle was 15 seconds, which is more than double the dwell times at each of the maximum and minimum temperatures due to the limits of the apparatus in changing temperature. Amplification and qSTAR product detection were performed with the Agilent Mx3005P qPCR apparatus (Agilent).

Results

Figure 15:
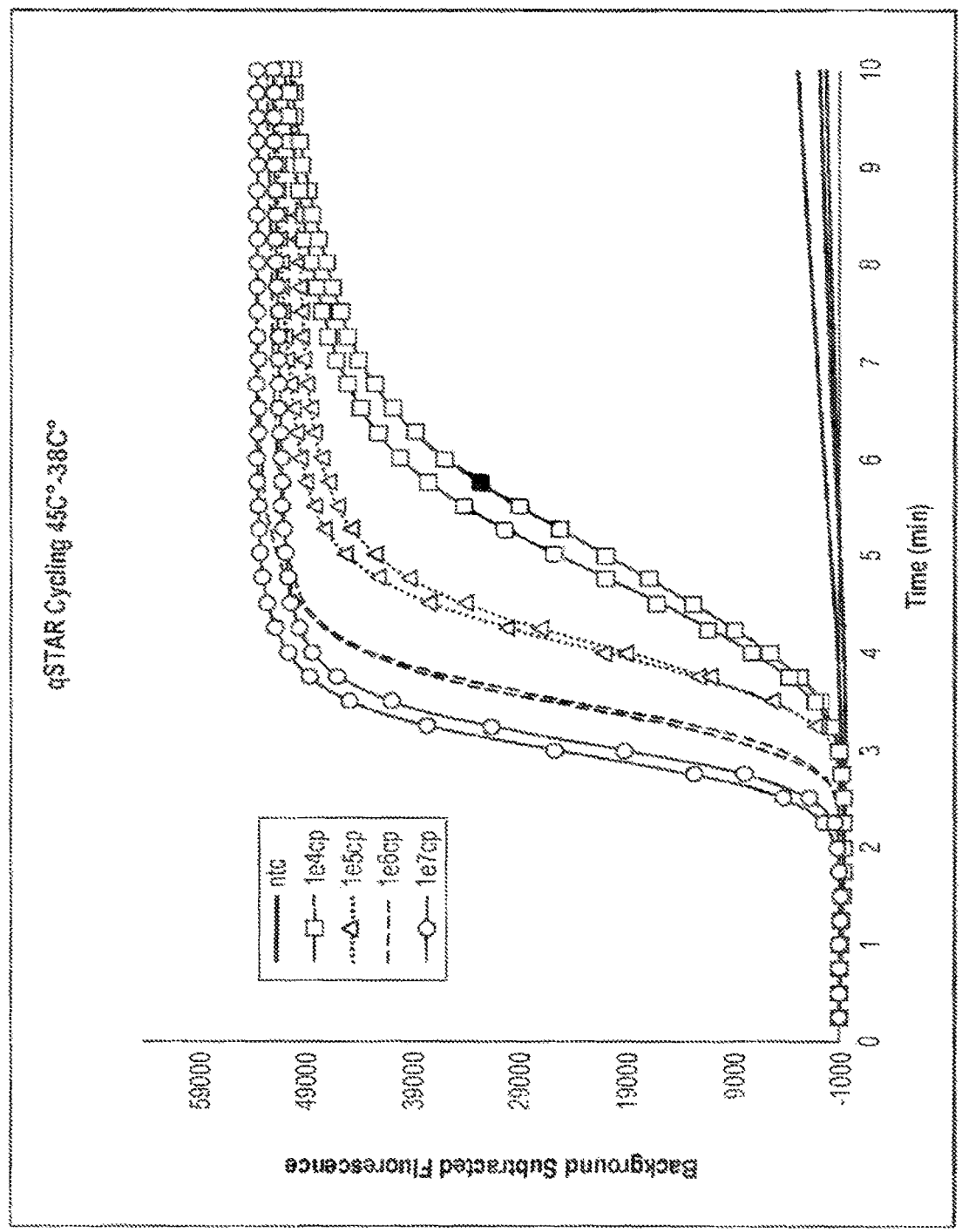
FIG. 15 is a graph of fluorescence (arbitrary units) against time (minutes), showing the results of amplification reactions performed according to the method of the invention at temperatures in the range 38-45° C.

FIG. 15 shows real time quantitative data for qSTAR amplifying in the above referenced range. The first thing that should be noticed is that, in this example, compared to the preceding examples the temperature phases have been switched: the higher temperature phase is for exponential amplification, in which both enzymes are active, while the lower temperature is for initiation, in which the polymerase is highly active and the nicking enzyme is relatively inhibited. The temperature difference between qSTAR and such "low temperature" qSTAR is 24° C. It is surprising and unexpected that a technology can work over such a large range of temperatures and further demonstrates that this amplification method is unlike any amplification method known previously, to the best knowledge of the inventors.

Not to limit the inventors to any particular theory, it is believed that qSTAR is able still to achieve amplification at these low temperatures because the nicking enzyme activity is greatly reduced at the lower temperature. This gating of enzymes allows for controlled and precise amplification of templates and the inventors can envisage many ways in which multiple enzymes, primers, and temperature schemes can be used in a single reaction to achieve new, fast, and quantitative results.

Example 10: Results Using Ribonucleic Acid qSTAR can amplify from any nucleic acid, using any composition of DNA (cDNA and gDNA), RNA (mRNA, tRNA, rRNA, siRNA, microRNA), RNA/DNA analogs, sugar analogs, hybrids, polyamide nucleic acid, and other known analogs. Amplification of ribosomal RNA was carried out as described below.

Enzymes, Oligonucleotides, and Target:

*Listeria monocytogenes* was used as the target for the development of a qSTAR RNA assay. *Listeria monocytogenes* (ATCC VR-886) genomic DNA was acquired from American Type Culture Collection (Manassas, Va.). Initial screening was performed on gDNA, and a 23S region of ribosomal RNA was found to be amplified with primers LMONF72 ACAC 5-OM (SEQ ID NO: 14, 5'-GGACTCGACACCGAGTCCAGTTACGATTmTmGmTmTmG-3') and LMONR86 ATAT (SEQ ID NO: 15, 5'-gGACTC-CATATGGAGTCCTACGGCTCCGCTTTT-3'). The resulting DNA template was detected using a molecular beacon LMONMB1 (SEQ ID NO: 16, 5'-FAM/gctgcGTTCCAAT-TCGCCTTTTTCGCagc/BHQ1-3') as described in EP No. 0728218.

Total RNA was isolated using the RNEASY® Plus mini kit Qiagen (Hilden, Germany) combined with rapid mechanical lysis on a Mini Bead Mill 4 (VWR). *Listeria monocytogenes* (ATCC BAA-2660) was acquired from American Type Culture Collection (Manassas, Va.), and revived by plating on brain-heart infusion agar plates (BHI). A single colony was used to inoculate 25 mL of BHI media that was grown for 18 hours at 37° C. to reach stationary phase. The culture was then back-diluted into two 50 mL portions of BHI in 250 mL flasks and grown for an additional four hours prior to harvest. Bacteria were harvested from two 30 mL aliquots of the back-diluted culture at 5,000×g for 15 min. The pellets were resuspended and combined into 5 mL of RNALATER™ RNA stabilization Reagent (Qiagen) and allowed to incubate for 10 min at room temperature. The bacteria were harvested and resuspended in 5 mL of RLT lysis buffer Bacteria, and homogenised on the Mini Bead Mill (VWR) at setting 5 (3×30 seconds with one minute on ice between pulses).

Total RNA was purified per manufacturer's directions (Qiagen). Genomic DNA was removed by passing lysates over a DNA-binding column provided in the RNEASY® Plus purification kit. Genomic DNA contamination was further reduced by utilizing an on-column RNase free DNase I (Qiagen) digestion of samples on the RNEASY® RNA-binding column. Bst X DNA Polymerase was purchased from Beverly Qiagen (Beverly, Mass.). OMNIS-CRIPT®, a Reverse Transcriptase, was purchased from Qiagen (Hilden, Germany). Nt.BstNBI nicking endonuclease was purchased from New England BioLabs (Ipswich, Mass.) as described in U.S. Pat. No. 6,191,267. Oligonucleotides and molecular beacons were synthesized by Integrated DNA Technologies (Coralville, Iowa).

Amplification Conditions:

The basic qSTAR mixture contained everything as described in example 1 above with the additional inclusion of the following: 4U of Reverse Transcriptase (referenced above).

Results

Figure 16:
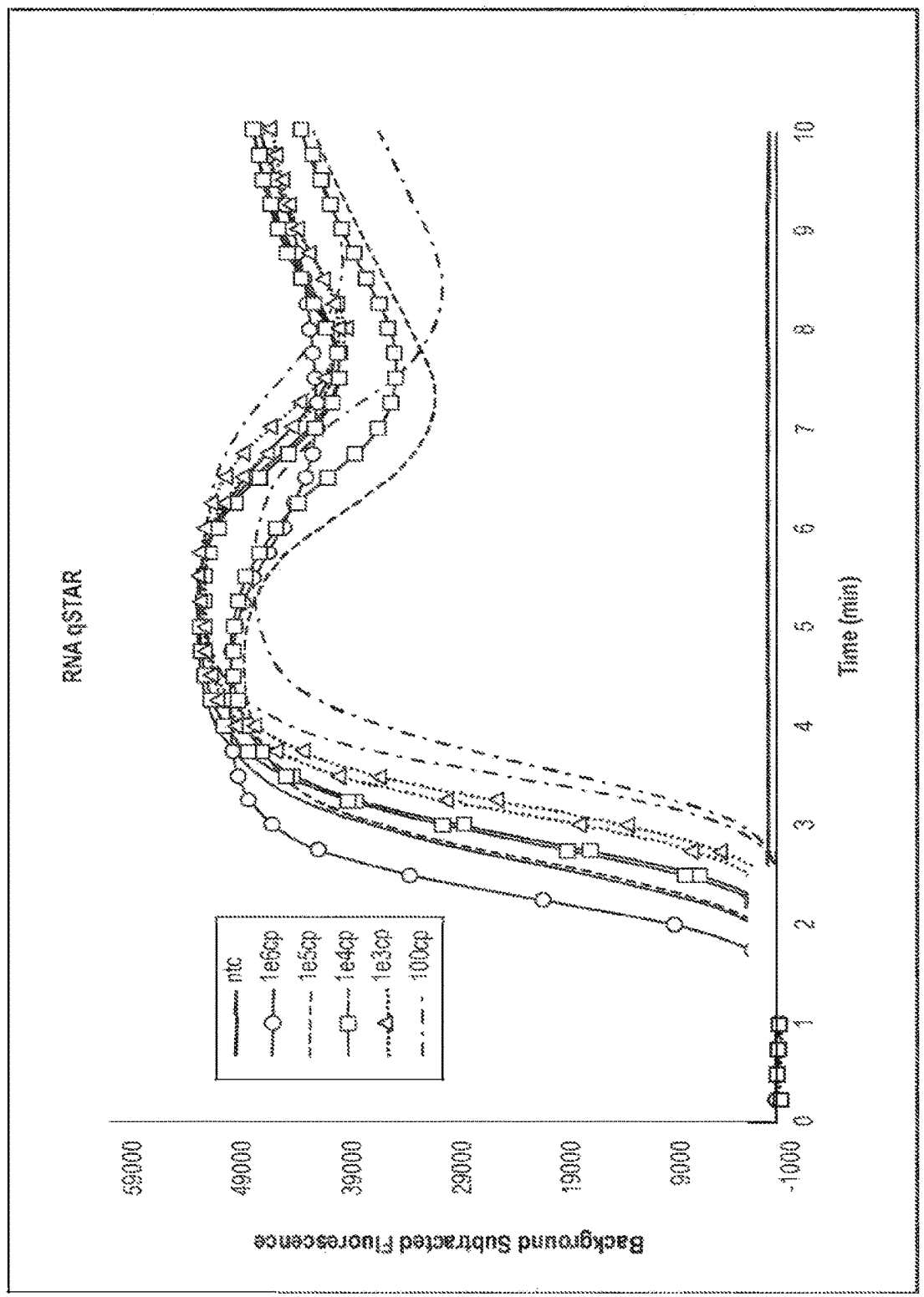
FIG. 16 is a graph of fluorescence (arbitrary units) against time (minutes), showing the results of amplification reactions performed according to the method of the invention, using a reverse transcribed RNA target sequence.

The results are shown in FIG. 16 which is a graph of fluorescence (arbitrary units) against time (minutes). Negative control reactions did not generate any fluorescence signal, whereas 100, 1,000, 10,000, 100,000, 1,000,000 copy number target reactions generated fluorescence signal above threshold. The results show that qSTAR can amplify effectively from a reverse transcribed RNA target. Furthermore the data indicates it could be used to quantitate unknown RNA sample inputs.

The invention claimed is:

1. A method of performing a non-isothermal nucleic acid amplification reaction, the method comprising the steps of:
   a) mixing a target sequence with one or more complementary single-stranded primers in conditions which permit a hybridization event in which the one or more primers hybridizes to the target, which hybridization event, directly or indirectly, leads to the formation of a duplex structure comprising two nicking sites disposed at or near opposite ends of the duplex; and performing an amplification process by;
   b) using a nicking enzyme to cause a nick at each of said nicking sites in the strands of the duplex;
   c) using a polymerase to extend the nicked strands so as to form newly synthesized nucleic acid, wherein extension with the polymerase recreates the nicking sites; and
   d) repeating steps (b) and (c) as desired so as to cause the production of multiple copies of the newly synthesized nucleic acid;
   wherein the temperature at which the method is performed is non-isothermal, and subject to shuttling, a plurality of times, between an upper temperature and a lower temperature during the amplification process of steps (b)-(d), and
   wherein at the upper temperature, one of said polymerase or nicking enzyme is more active than the other of said enzymes, such that there is a disparity in the activity of the enzymes, and at the lower temperature the disparity in the activity of the enzymes is reduced or reversed.

2. The method according to claim 1, wherein in step (a) the target comprises two complementary strands of nucleic acid, and the method uses forward and reverse primers which are each complementary to a respective strand of the target, such that the 3' ends of the forward and reverse primers are oriented towards each other.

3. The method according to claim 1, wherein steps (b)-(d) are performed substantially immediately after step (a), and wherein steps (a)-(d) are performed in the same reaction vessel or on the same solid support.

4. The method according to claim 1, further comprising the step of detecting, directly or indirectly, the newly synthesized nucleic acid.

5. The method according to claim 4, wherein said detecting step comprises the use of a molecular beacon or a fluorescent dye, a lateral flow labelled probe, or an enzyme which catalyzes an electrochemical reaction.

6. The method according to claim 1, wherein the amount of newly synthesized nucleic acid is quantified or measured during the performance of the amplification reaction.

7. The method according to claim 6, wherein the amount of newly synthesized nucleic acid is used to determine the amount and/or concentration of the target sequence in a quantitative manner.

8. The method according to claim 1, wherein the upper temperature relatively favors the activity of the polymerase.

9. The method according to claim 1, wherein the upper temperature relatively favors the activity of the nicking enzyme.

10. The method according to claim 1, wherein the optimum temperature of the polymerase differs from the optimum temperature of the nicking enzyme by an amount in the range 10-30° C.

11. The method according to claim 1, wherein the upper temperature is in the range 50-64° C.

12. The method according to claim 1, wherein the lower temperature is in the range 20.0-58.5° C.

13. The method according to claim 1, wherein the temperature shuttling is performed continuously for a plurality of shuttles and over a period of at least two minutes.

14. The method according to claim 1, wherein each of the plurality of shuttles is substantially identical.

15. The method according to claim 1, wherein each of the plurality of temperature shuttles has a duration in the range 5-60 seconds.

16. The method according to claim 1, wherein each of the plurality of temperature shuttles has a dwell time at the upper temperature in the range 1-10 seconds.

17. The method according to claim 1, wherein each of the plurality of temperature shuttles has a dwell time at the lower temperature in the range 2-40 seconds.

18. The method according to claim 1, wherein each of the plurality of temperature shuttles has a transition time between the lower temperature and the upper temperature in the range 0.5-10 seconds.

19. The method according to claim 1, wherein step (a) is preceded by performing a reverse transcription step, comprising contacting an RNA analyte of interest with a reverse transcriptase so as to form a DNA transcript of the RNA analyte of interest, said DNA transcript comprising the target sequence.

20. The method according to claim 19, further comprising the step of making double-stranded DNA from the DNA transcript.

21. The method according to claim 1, further comprising a pre-amplification or enrichment step.

22. The method according to claim 1, wherein at least one of the one or more primers comprises a modified nucleotide.

23. The method according to claim 22, wherein at least one of the one or more primers comprises a 2'-modified nucleotide.

24. The method according to claim 23, wherein at least one of the one or more primers comprises up to seven 2'-O-methyl modified nucleotides.

25. The method according to claim 1, wherein one or more primers comprises a self-complementary portion forming a hairpin structure comprising 5 to 10 base pairs.

26. A method of determining the amount and/or concentration of a target polynucleotide in a sample, the method comprising the steps of: performing the amplification reaction of claim 1 to amplify the target polynucleotide in the sample; and detecting, in a quantitative manner, the direct or indirect product(s) of the amplification reaction, so as to allow a determination of the amount and/or concentration of the target polynucleotide in the sample.

\* \* \* \* \*